(12) United States Patent
Wormser

(10) Patent No.: US 9,518,107 B2
(45) Date of Patent: Dec. 13, 2016

(54) PHARMACEUTICAL COMPOSITIONS CONTAINING POLYPEPTIDES DERIVED FROM α-1 ANTITRYPSIN AND METHODS OF USE THEREOF

(71) Applicant: YISSUM RESEARCH DEVELOPMENT COMPANY OF THE HEBREW UNIVERSITY OF JERUSALEM, LTD., Jerusalem (IL)

(72) Inventor: Uri Wormser, Jerusalem (IL)

(73) Assignee: YISSUM RESEARCH DEVELOPMENT COMPANY OF THE HEBREW UNIVERSITY OF JERUSALEM, LTD., Jerusalem (IL)

( * ) Notice: Subject to any disclaimer, the term of this patent is extended or adjusted under 35 U.S.C. 154(b) by 0 days.

(21) Appl. No.: 14/628,644

(22) Filed: Feb. 23, 2015

(65) Prior Publication Data
US 2015/0239955 A1 Aug. 27, 2015

Related U.S. Application Data

(63) Continuation-in-part of application No. 13/819,669, filed as application No. PCT/IL2011/000696 on Aug. 30, 2011, now abandoned.

(60) Provisional application No. 61/425,038, filed on Dec. 20, 2010, provisional application No. 61/378,414, filed on Aug. 31, 2010.

(51) Int. Cl.
*A61K 38/55* (2006.01)
*C07K 14/81* (2006.01)

(52) U.S. Cl.
CPC ........... *C07K 14/8125* (2013.01); *A61K 38/55* (2013.01)

(58) Field of Classification Search
CPC ..................... A61K 38/55; C07K 14/8125
USPC ........ 424/93.1, 93.4, 93.51, 93.7; 435/252.3, 435/254.2, 320.1, 325, 348; 514/17.8, 514/17.9, 18.6, 1.4, 1.7, 21.3, 44 R; 530/324; 536/23.5
See application file for complete search history.

(56) References Cited

U.S. PATENT DOCUMENTS

| | | |
|---|---|---|
| 5,093,316 A | 3/1992 | Lezdey |
| 5,134,119 A | 7/1992 | Lezdey |
| 6,537,968 B1 | 3/2003 | Lezdey |
| 7,419,670 B2 | 9/2008 | Zhong |
| 2008/0095806 A1 | 4/2008 | Bathurst |
| 2008/0261868 A1 | 10/2008 | Shapiro |

FOREIGN PATENT DOCUMENTS

| | | |
|---|---|---|
| EP | 2105740 A1 | 9/2009 |
| JP | 2010/190804 A | 9/2010 |
| WO | 9206706 A1 | 4/1992 |
| WO | 03/058021 A2 | 7/2003 |
| WO | 2005090387 A2 | 9/2005 |
| WO | 2006/091773 A2 | 8/2006 |
| WO | 2009074350 A2 | 6/2009 |
| WO | 2010054192 A2 | 5/2010 |

OTHER PUBLICATIONS

Berns et al., "Adenovirus and Adeno-Associated Virus as Vectors for Gene Therapy", Annals New York Academy of Sciences, 1995, pp. 95-104.
Federoff et al., "Expression of nerve growth factor in vivo from a defective herpes simplex virus1 vector prevents effects of axotomy on sympathetic ganglia", Proc. Natl. Acad. Sci. USA, 1992, vol. 89, pp. 1636-1640.
Fink et al., "Gene Transfer to Neurons Using Herpes Simplex Virus-Based Vectors", Annu. Rev. Neurosci., 1996, vol. 19, pp. 265-287.
Merrifield, "Solid Phase Peptide Synthesis. I. The Synthesis of a Tetrapeptide," 1963, J. of American Chemical Society, vol. 85, pp. 2149-2154.
Schur, "Systemic Lupus Erythematosus", Cecil Textbook of Medicine, 2nd Ed., 2004, CH.280, pp. 1660-1670.
Shapira et al., "Novel peptides as potential treatment of systemic lupus erythematosus", Lupus, 2011, vol. 20, pp. 463-472.

*Primary Examiner* — Julie Ha
(74) *Attorney, Agent, or Firm* — Lucas & Mercanti, LLP

(57) ABSTRACT

Isolated polypeptides comprising the amino acid sequence of residues 378-413 of *Mus musculus* α-1-antitrypsyn (serpin A1c),active fragments thereof, and pharmaceutical compositions comprising same are described. The compositions are useful for treating burns, inflammatory, autoimmune and degenerative diseases.

23 Claims, 27 Drawing Sheets

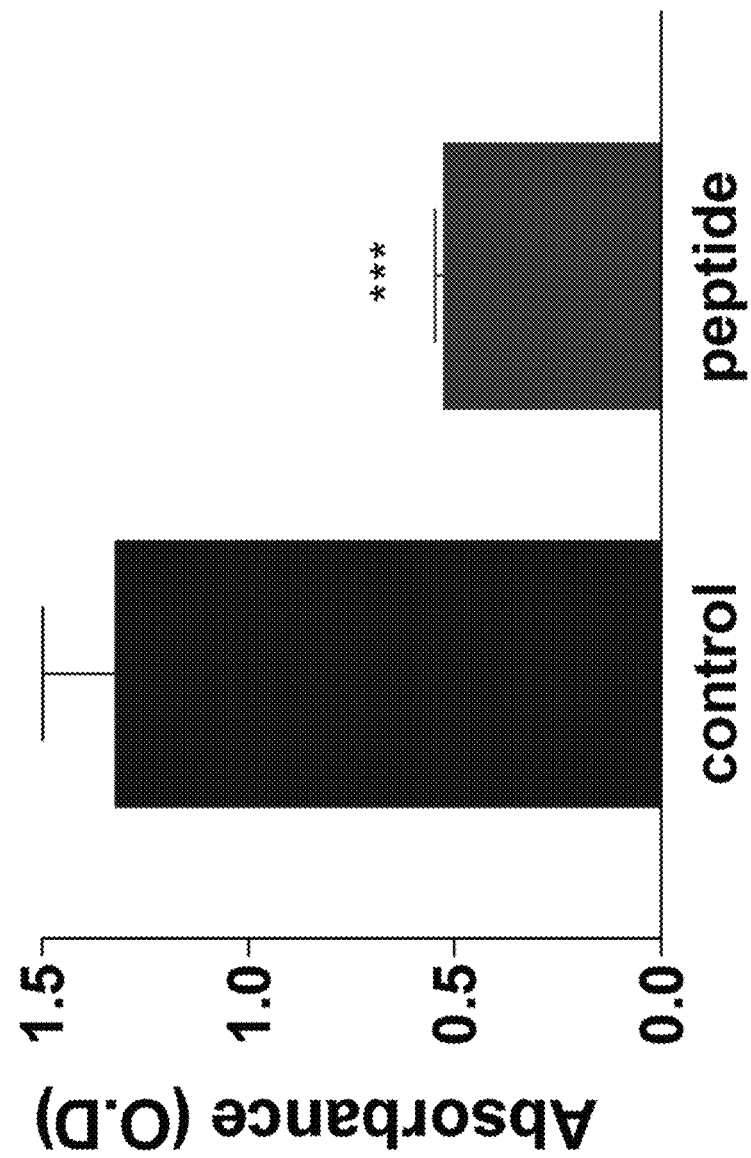

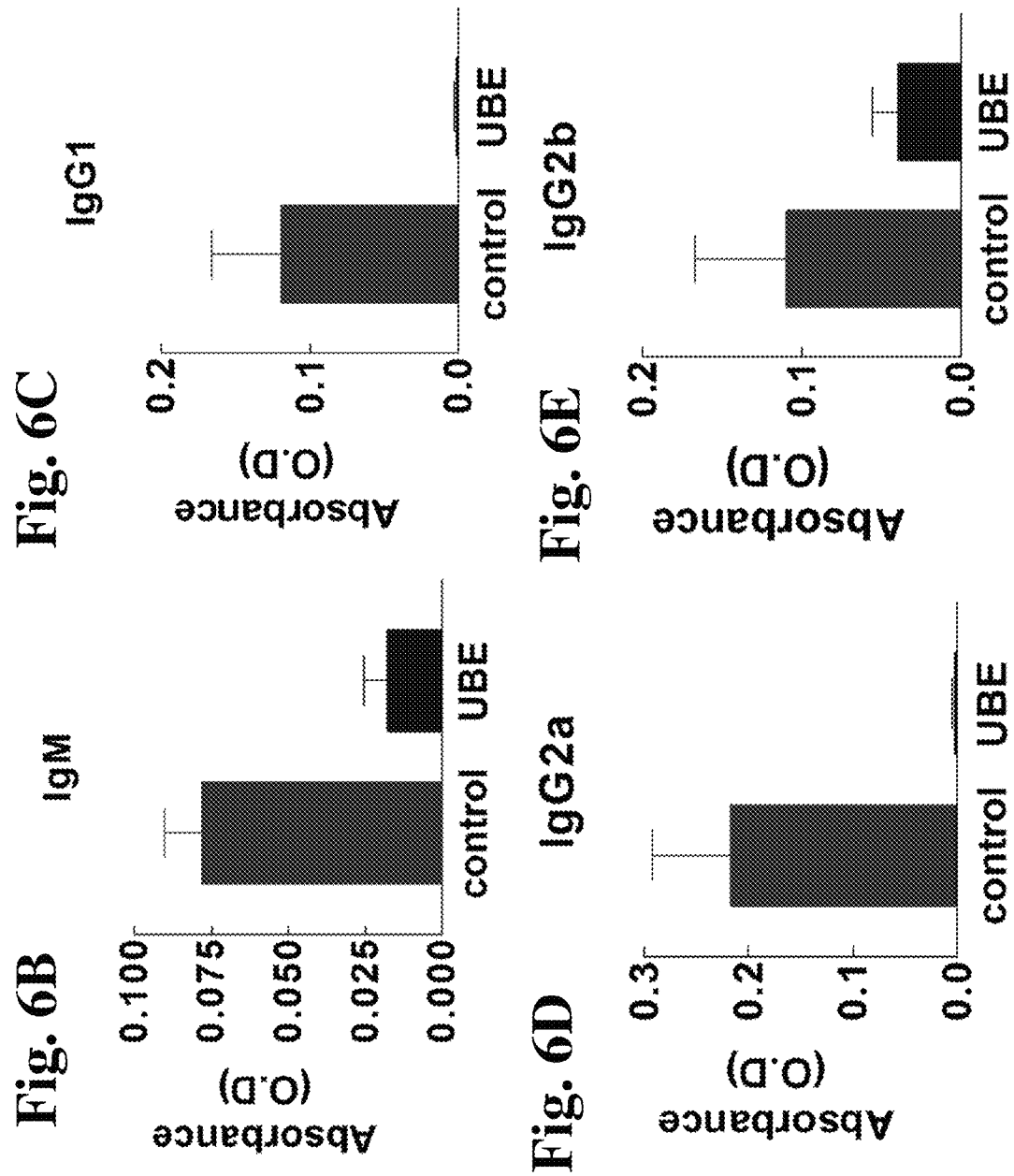

control x20

UBE x20 control x2

UBE x2

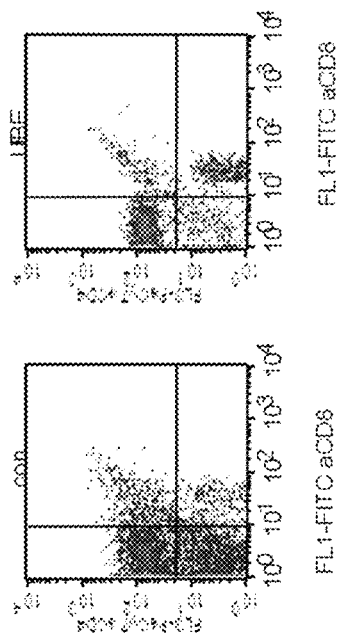
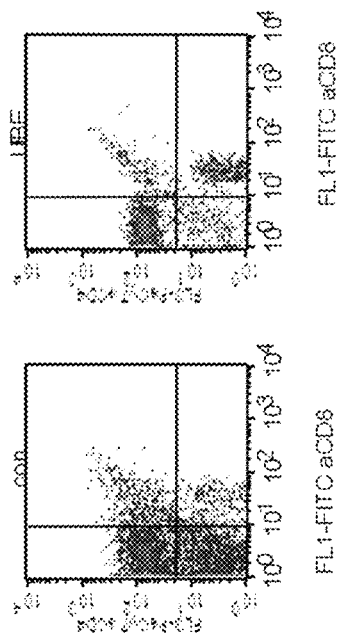
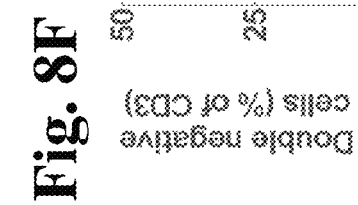
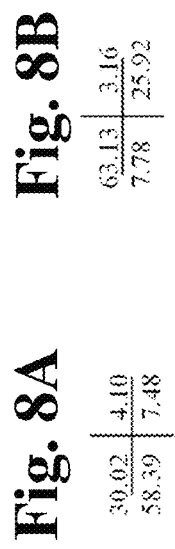
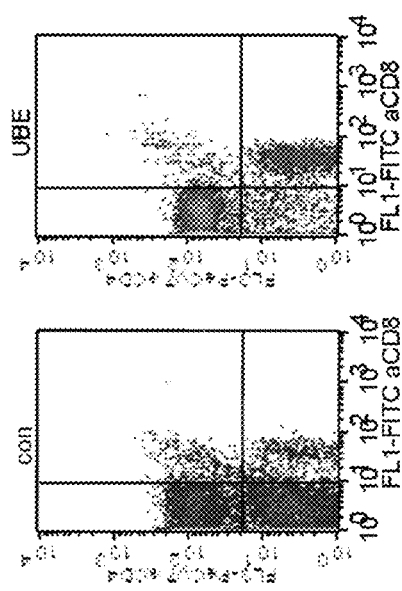
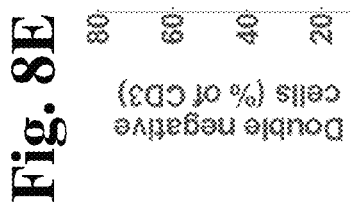

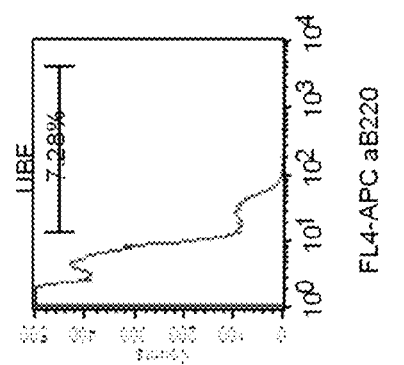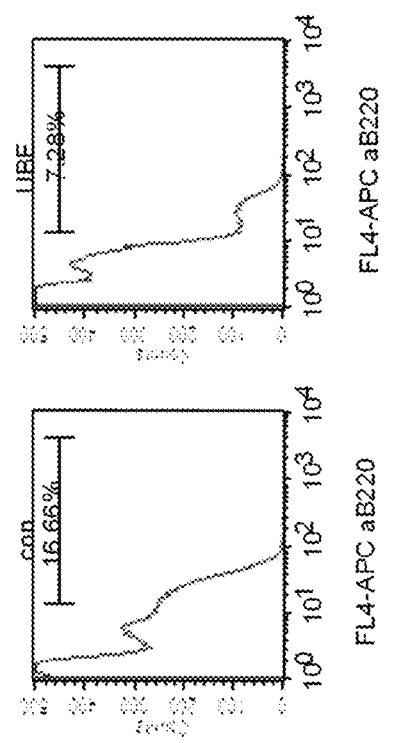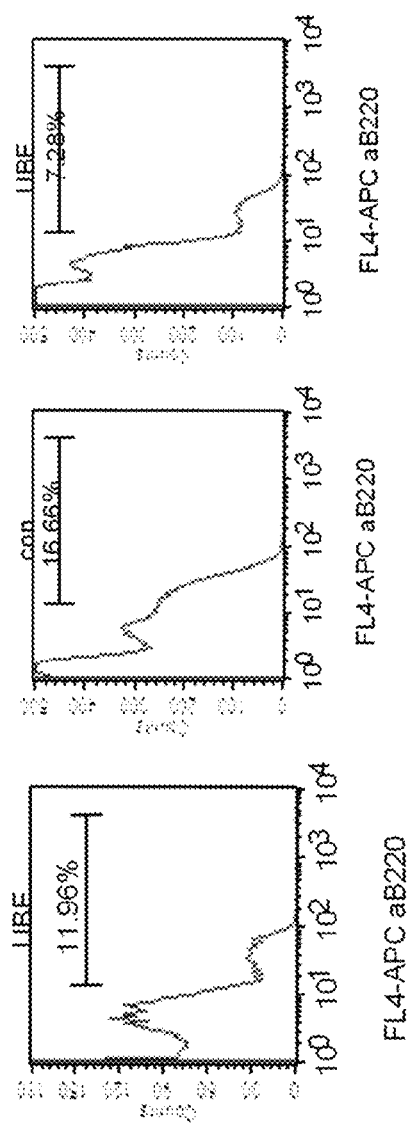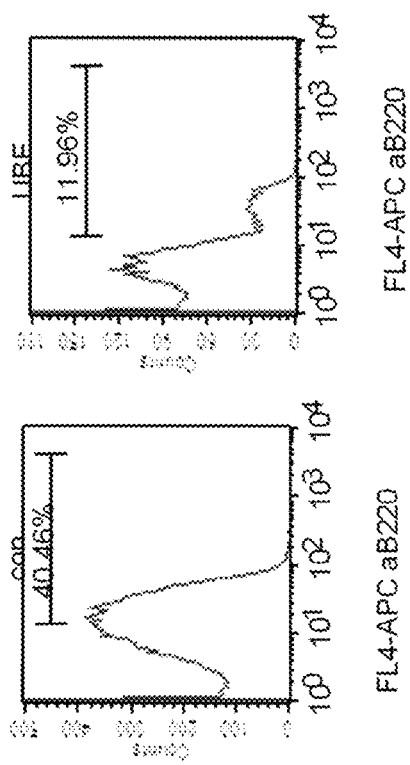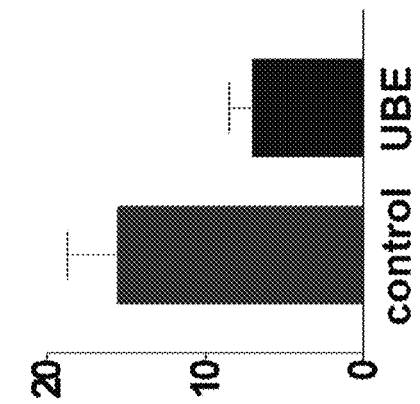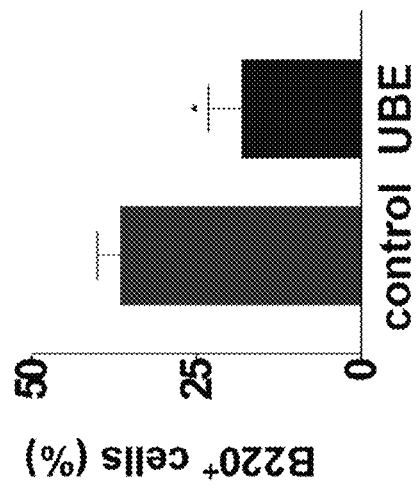

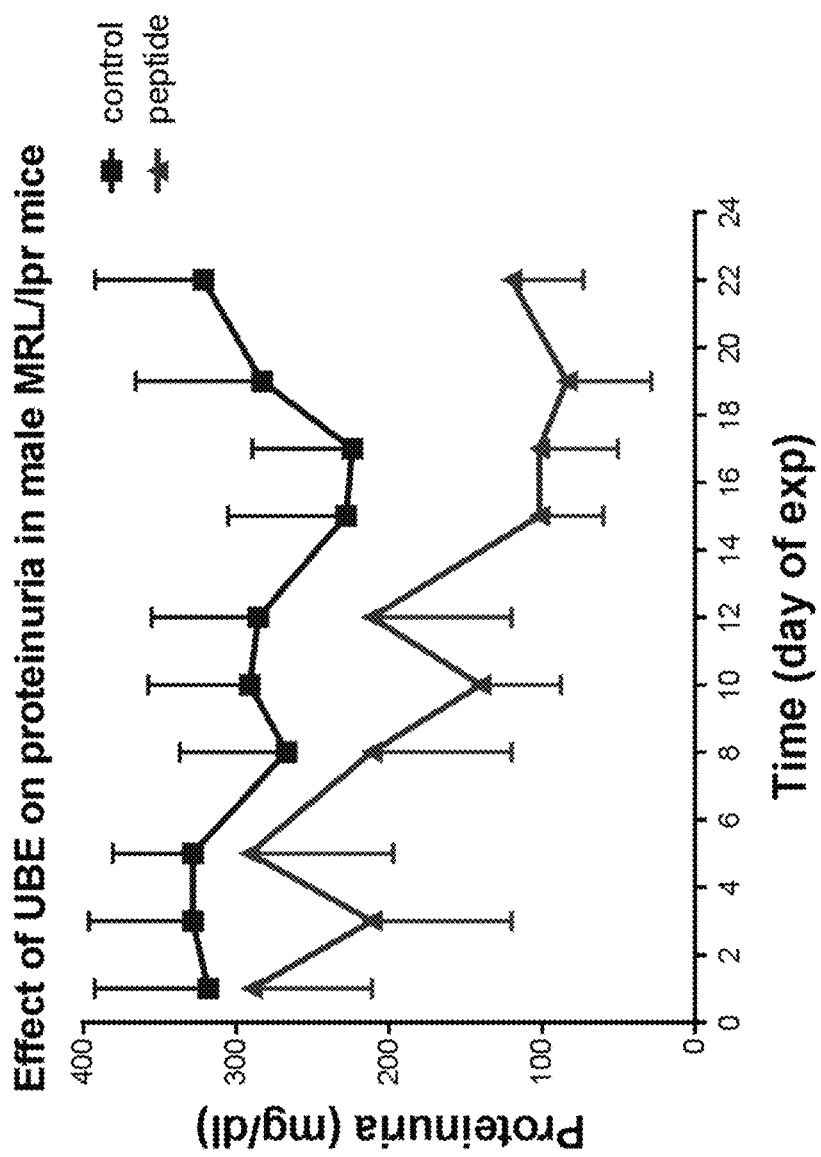

Effect of UBE on interstitial damage

Effect of UBE on tubular damage

Effect of UBE on serum Blys levels

Effect of UBE on serum levels of double strand DNA antibodies

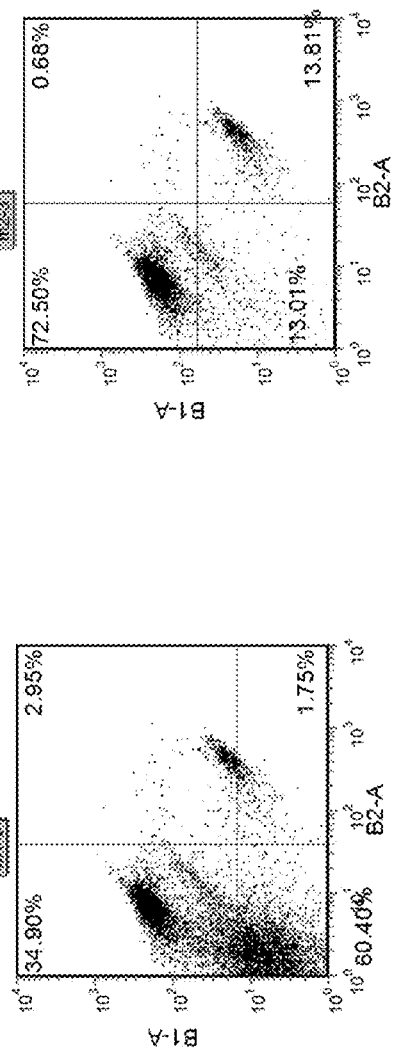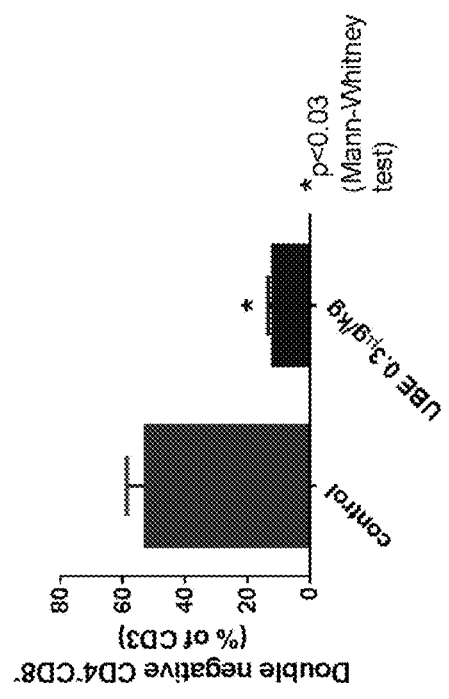
Fig. 14A
Fig. 14B
Fig. 14C Effect of UBE on spleen double negative CD4⁻CD8⁻

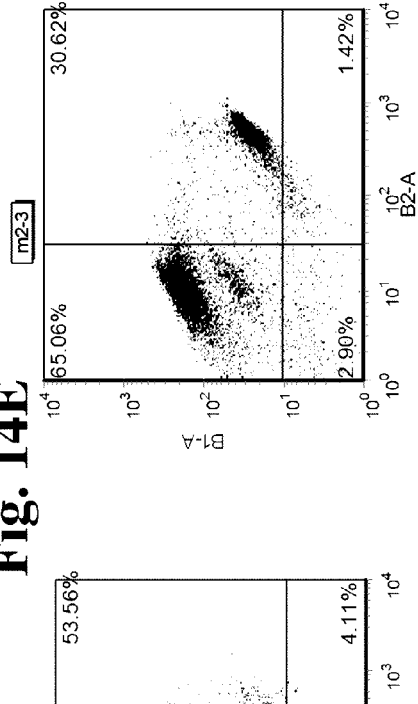
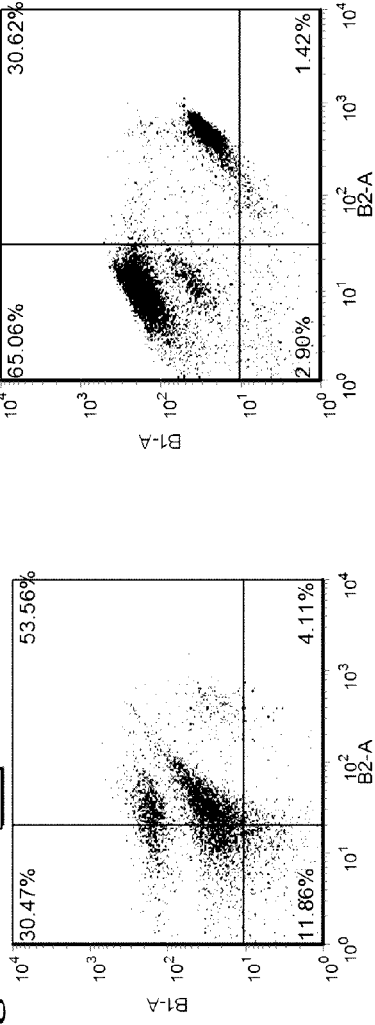
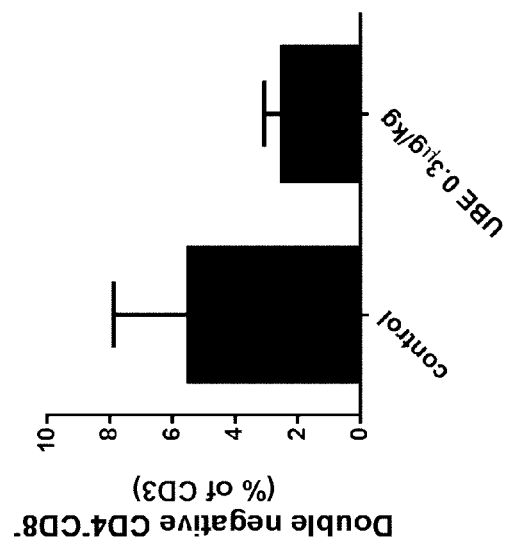
Fig. 14D
Fig. 14E
Fig. 14F

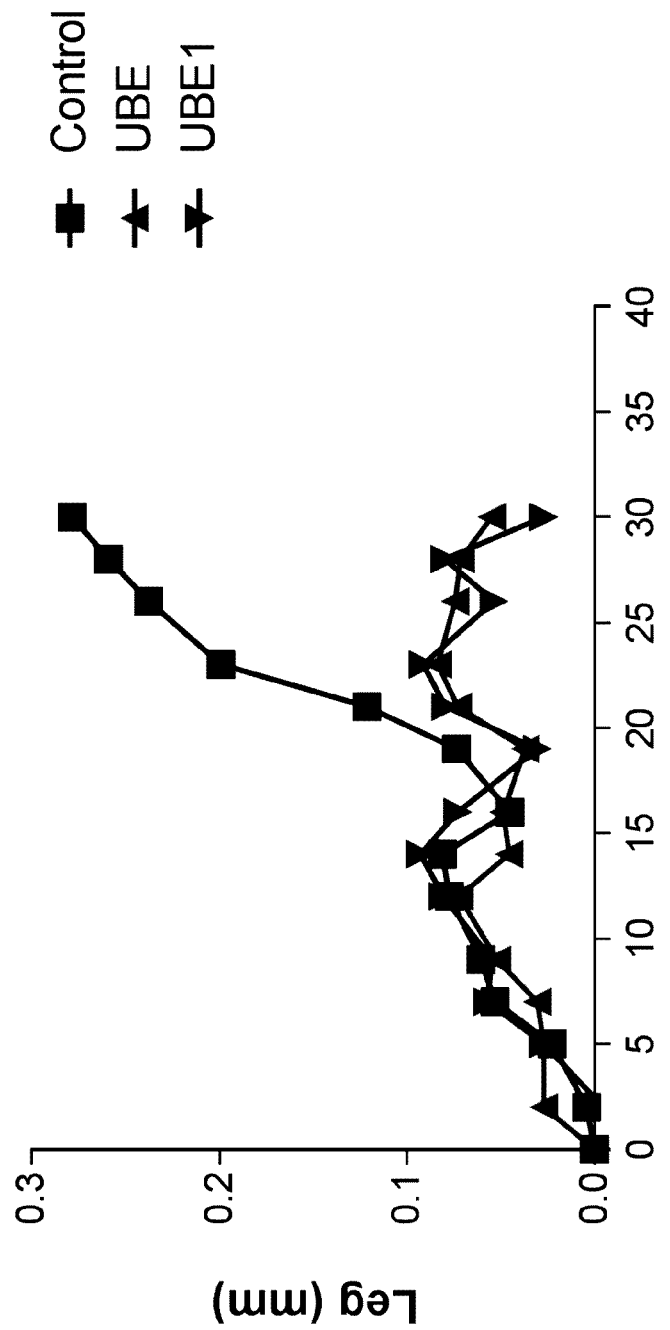

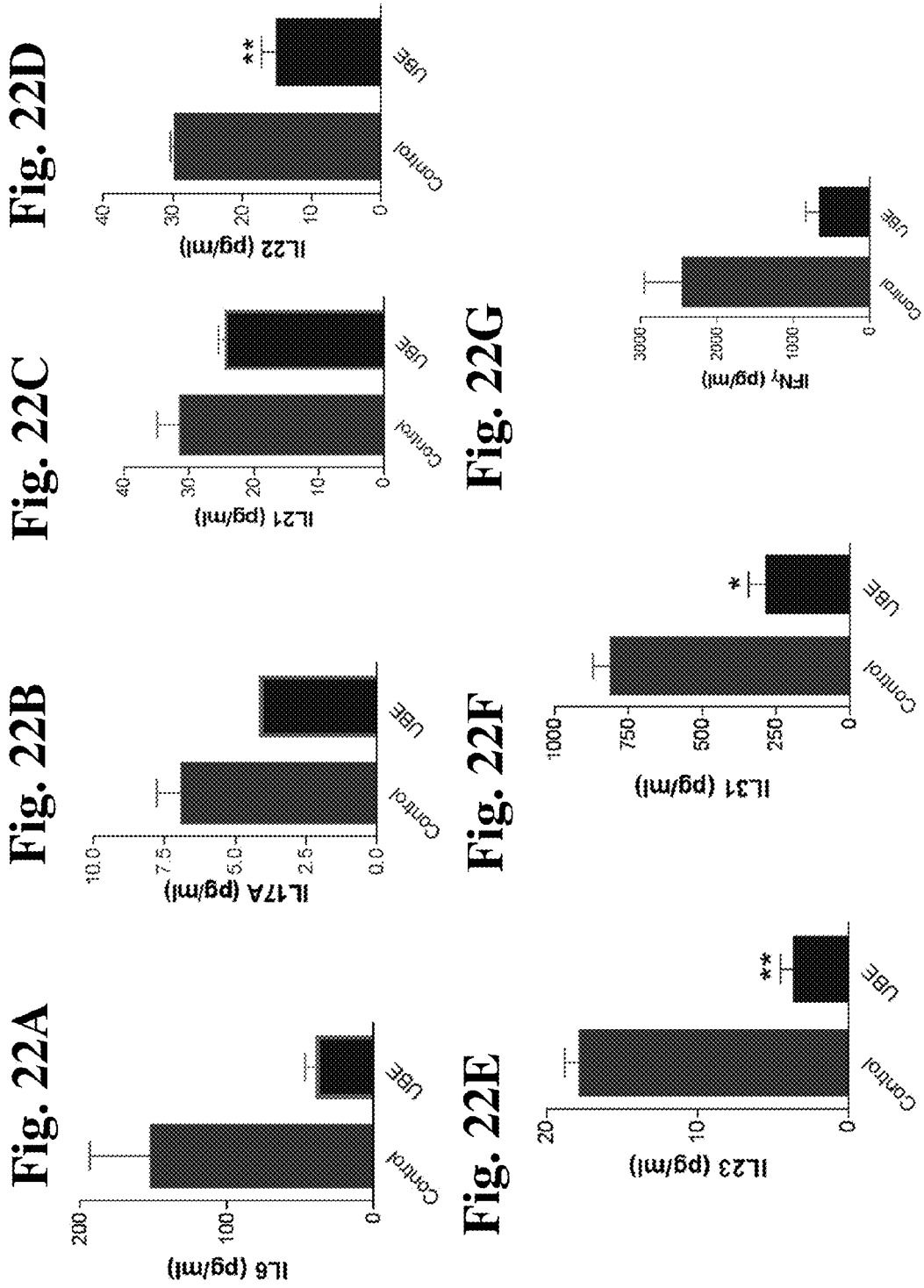

```
                        SEQUENCE LISTING

<160> NUMBER OF SEQ ID NOS: 4

<210> SEQ ID NO 1
<211> LENGTH: 37
<212> TYPE: PRT
<213> ORGANISM: Mus musculus

<400> SEQUENCE: 1

Tyr Ser Met Pro Pro Ile Val Arg Phe Asp His Pro Phe Leu Phe Ile
1               5                   10                  15

Ile Phe Glu Glu His Thr Gln Ser Pro Leu Phe Val Gly Lys Val Val
            20                  25                  30

Asp Pro Thr His Lys
        35

<210> SEQ ID NO 2
<211> LENGTH: 36
<212> TYPE: PRT
<213> ORGANISM: Mus musculus

<400> SEQUENCE: 2

Ser Met Pro Pro Ile Val Arg Phe Asp His Pro Phe Leu Phe Ile Ile
1               5                   10                  15

Phe Glu Glu His Thr Gln Ser Pro Leu Phe Val Gly Lys Val Val Asp
            20                  25                  30

Pro Thr His Lys
        35

<210> SEQ ID NO 3
<211> LENGTH: 35
<212> TYPE: PRT
<213> ORGANISM: Mus musculus

<400> SEQUENCE: 3

Met Pro Pro Ile Val Arg Phe Asp His Pro Phe Leu Phe Ile Ile Phe
1               5                   10                  15

Glu Glu His Thr Gln Ser Pro Leu Phe Val Gly Lys Val Val Asp Pro
            20                  25                  30

Thr His Lys
        35
```

```
<210> SEQ ID NO 4
<211> LENGTH: 35
<212> TYPE: PRT
<213> ORGANISM: Mus musculus

<400> SEQUENCE: 4

Ser Met Pro Pro Ile Val Arg Phe Asp His Pro Phe Leu Phe Ile Ile
1               5                   10                  15

Phe Glu Glu His Thr Gln Ser Pro Leu Phe Val Gly Lys Val Val Asp
            20                  25                  30

Pro Thr His
        35
```

PHARMACEUTICAL COMPOSITIONS CONTAINING POLYPEPTIDES DERIVED FROM α-1 ANTITRYPSIN AND METHODS OF USE THEREOF

CROSS-REFERENCE TO RELATED APPLICATIONS

This application is a Continuation-in-part application of U.S. patent application Ser. No. 13/819,669, filed Apr. 22, 2013, which is a 371 National Stage filing of PCT International Application Number PCT/IL2011/000696, filed Aug. 30, 2011, which claims the benefit of U.S. Provisional Patent Application Nos. 61/378,414, filed Aug. 31, 2010 and 61/425,038, filed Dec. 20, 2010, the contents of each of which are incorporated herein by reference.

FIELD OF INVENTION

The present invention relates to isolated polypeptides comprising the amino acid sequence of residues 378-413 of *Mus musculus* endogenous α-1-antitrypsin (serpin a1c) and to pharmaceutical compositions comprising same useful for treating inflammatory, autoimmune and degenerative diseases

BACKGROUND OF THE INVENTION

Systemic Lupus Erythematosus (SLE) is a disease that can produce fever, rash, hair loss, arthritis, pleuritis, pericarditis, nephritis, anemia, leucopenia, thrombocytopenia and central nervous system damage. The clinical course is characterized by periods of remissions and acute or chronic relapses. Characteristic immune abnormalities, especially antibodies to nuclear and other cellular antigens, develop in patients with SLE (Schur P H, systemic lupus erythematosus, in Cecil textbook of Medicine, 22nd edition, Editors: Goldman L, Ausiello D, Saunders, USA, 2004, pp 1660-1670).

SLE occurs more frequently in women. The female to male ratio ranges from 10:1 to 15:1 in adults and in other individuals it is 8:1. Among the general population the prevalence is estimated to be 40-50 per 100,000. The cause of SLE remains unknown in spite of many observations on the involvement of genetic, immunologic, hormonal and environmental factors. SLE is primarily a disease with abnormalities of immune system regulation. These abnormalities are secondary to a loss of self tolerance, resulting in autoimmune responses. Due to decreased number of regulatory (suppressor) T cells which control the immune response, the immune response against self components increases, causing activation and proliferation of autoreactive B cells which differentiate into antibody-producing cells and make an excess of antibodies to many nuclear antigens. Anti nuclear antibodies are elevated especially to dsDNA, ssDNA, nucleoproteins and other self components. In addition, female hormones promote B-cell hyperactivity while androgens have the opposite effect. Environmental factors like microorganisms may stimulate cells in the immune system. Ultraviolet irradiation is known to exacerbate lupus skin lesions.

The pathogenesis of SLE includes many manifestations, which are mediated by antibodies. Diffuse proliferative glomerulonephritis is caused by immune complexes, which consist of nuclear antigens and antinuclear antibodies, formed in the circulations and deposited in the glomerular basement membrane or formed in situ. This activates the complement system resulting in the generation of chemotactic factors causing attraction and infiltration of leukocytes which phagocytose the immune complexes and cause the release of mediators which further perpetuate the glomerular inflammation. Deposition of immune complexes leads to chronic inflammation, fibrinoid necrosis and scarring, and renal dysfunction (Schur P H, systemic lupus erythematosus, in Cecil textbook of Medicine, 22nd edition, Editors: Goldman L, Ausiello D, Saunders, USA, 2004, pp 1660-1670). Immune complexes have been detected at the dermal-epidermal junction in skin lesions and normal skin, in the choroid plexus, pericardium and pleural cavity.

The pathological symptoms of SLE include renal disease, musculoskeletal manifestations such as arthralgia and arthritis, mucocutaneous lesions including photosensitivity, rash and discoid lesions, vascular, cardiovascular and pulmonary lesions, hematologic manifestations, gastrointestinal and neuropsychiatric disturbances, and general symptoms like sleep disturbances and depression. Drug therapy is mainly based on steroids (prednisone) and immunosuppressants (cyclophosphamide, azathioprine). The prognosis of SLE patients has improved during the last 50 years i.e. the current survival rate is approximately 90% at 10 years. Nevertheless, there are side effects of the medicaments associated with poor quality of life and, in 10% of the cases a bad prognosis is anticipated especially in CNS involvement, hypertension, azotemia and early age of onset.

U.S. Pat. No. 6,537,968 discloses a method for treating lupus erythematosus comprising administering a therapeutically effective amount of a composition containing a protease inhibitor selected from a group consisting of alpha 1-antitrypsin, secretory leukocyte protease inhibitor and alpha 2-macroglobulin.

U.S. Pat. No. 7,419,670 discloses viral protein SERP-1, SERP-1 analogs or biologically active fragments, which are useful for treating inflammatory or immune reaction associated with arthritis, systemic lupus erythematosus (SLE), multiple sclerosis (MS) and asthma. While U.S. Pat. No. 7,419,670 claims methods of treating a mammalian subject having arthritis, systemic lupus erythematosus (SLE), multiple sclerosis (MS) and asthma the polypeptides disclosed are useful only when administered in combination with an immunosuppressant.

U.S. Patent Application No. 2008/0261868 provides a method of treating a subject suffering from a disease characterized by excessive apoptosis by administering at least one serine protease inhibitor, preferably alpha 1-antitrypsin or a derivative thereof.

U.S. Patent Application No. 2008/0095806 discloses protease inhibitor composition useful for preventing and treating hyperproliferative and inflammatory mucocutaneous disorders. U.S. Patent Application No. 2008/0095806 claims methods of treating hyperproliferative and inflammatory mucocutaneous disorders comprising administering to the subject an effective amount of protease inhibitor in a pharmaceutically acceptable carrier or diluent. According to U.S. Patent Application No. 2008/0095806, the protease inhibitor is preferably a serine protease inhibitor, and more preferably alpha 1-antitrypsin including peptide fragments and derivatives thereof useful for preventing and treating hyperproliferative and inflammatory mucocutaneous. Nonetheless there is no indication of specific peptide fragments derived from alpha 1-antitrypsin.

U.S. Pat. No. 5,093,316 discloses a method and pharmaceutical compositions for treating pulmonary inflammation in pulmonary diseases comprising administering an effective amount of microcrystalline alpha-1-antitrypsin, derivatives or salts thereof.

International Patent Application No. WO 9206706 provides use of an effective amount of alpha 1-antitrypsin among other serine protease inhibitors for the prophylaxis or treatment of a mast cell-implicated disease or injury in a mammal.

U.S. Pat. No. 5,134,119 discloses a method for prophylaxis or direct treatment of mast cell implicated skin inflammation or treating the symptoms of burns in a patient comprising administering an effective amount of an analog of alpha 1-antitrypsin. While U.S. Pat. No. 5,134,119 discloses various analogs of alpha 1-antitrypsin, the polypeptides are useful for treatment of mast cell implicated skin inflammation only when methionine at position 358 is substituted with an aliphatic amino acid.

There is still an unmet need for improved medicaments for treating inflammatory and autoimmune diseases.

Severe sepsis occurs when the inflammatory reaction towards an infectious agent leads to organ dysfunction, such as trouble breathing, coagulation or other blood abnormalities, decreased urine production, or altered mental status. If the organ dysfunction of severe sepsis is low blood pressure (hypotension), or insufficient blood flow (hypoperfusion) to one or more organs (causing, for example, lactic acidosis), this condition is referred to as septic shock.

Sepsis can lead to multiple organ dysfunction syndrome (MODS) culminating in death. Organ dysfunction results from local changes in blood flow, from sepsis-induced hypotension (<90 mmHg or a reduction of ≥40 mmHg from baseline) and from diffuse intravascular coagulation, among other things.

Sepsis can be defined as the body's response to an infection caused by microorganisms or bacteria invading the body, and can be limited to a particular body region or can be widespread in the bloodstream. Sepsis is acquired quickest with infections that are developed during surgery and physical contact with someone with sepsis.

The therapy of sepsis rests on antibiotics, surgical drainage of infected fluid collections, fluid replacement and appropriate support for organ dysfunction. This may include hemodialysis in kidney failure, mechanical ventilation in pulmonary dysfunction, transfusion of blood products, and drug and fluid therapy for circulatory failure.

Most therapies aimed at the inflammation process itself have failed to improve outcome, however drotrecogin alfa (activated protein C, one of the coagulation factors) has been shown to decrease mortality from about 31% to about 25% in severe sepsis. To qualify for drotrecogin alfa, a patient must have severe sepsis or septic shock with an APACHE II score of 25 or greater and a low risk of bleeding. However, since further trials have failed to replicate this result, the use of activated protein C is controversial.

In some cases, sepsis may lead to inadequate tissue perfusion and necrosis. As this may affect the extremities, amputation may become necessary.

SUMMARY OF THE INVENTION

The present invention provides pharmaceutical compositions comprising isolated polypeptides diminishing or abrogating an inflammatory response in a subject and methods of use of such isolated polypeptides or compositions for treating diseases attributable to inflammatory processes including autoimmune diseases such as Systemic Lupus Erythematosus (SLE), multiple sclerosis (MS) and arthritis as well as inflammatory pathologies such as sepsis.

It is now disclosed for the first time that a 36-mer peptide designated herein below UBE of the amino acid sequence Ser-Met-Pro-Pro-Ile-Val-Arg-Phe-Asp-His-Pro-Phe-Leu-Phe-Ile-Ile-Phe-Glu-Glu-His-Thr-Gln-Ser-Pro-Leu-Phe-Val-Gly-Lys-Val-Val-Asp-Pro-Thr-His-Lys (SEQ ID NO: 2) corresponding to residues 378-413 of Mus Musculus alpha-1-antitrypsin (also designated serpin a1c) is highly effective in eliminating neurological damage in multiple sclerosis as well as in reducing various manifestations of systemic lupus erythematosus (SLE) and arthritis in animal models as well as increasing survival in an animal model of sepsis. It is further disclosed that a peptide designated herein below UBE1 of the amino acid sequence Tyr-Ser-Met-Pro-Pro-Ile-Val-Arg-Phe-Asp-His-Pro-Phe-Leu-Phe-Ile-Ile-Phe-Glu-Glu-His-Thr-Gln-Ser-Pro-Leu-Phe- Val-Gly-Lys-Val- Val-Asp-Pro-Thr-His-Lys (SEQ ID NO: 1) corresponding to residues 377-413 of Mus Musculus alpha-1-antitrypsin (serpin a1c) is highly effective in eliminating neurological damage in animal models of multiple sclerosis as well as in reducing joint swelling in arthritic animals.

It is yet further disclosed that a peptide designated herein below UBE-N of the amino acid sequence Met-Pro-Pro-Ile-Val-Arg-Phe-Asp-His-Pro-Phe-Leu-Phe-Ile-Ile-Phe-Glu-Glu-His-Thr-Gln-Ser-Pro-Leu-Phe-Val-Gly-Lys-Val-Val-Asp-Pro-Thr-His-Lys (SEQ ID NO: 3) corresponding to residues 379-413 of Mus Musculus alpha-1-antitrypsin (serpin a1c) and a peptide designated herein below UBE-C of the amino acid sequence Ser-Met-Pro-Pro-Ile-Val-Arg-Phe-Asp-His-Pro-Phe-Leu-Phe-Ile-Ile-Phe-Glu-Glu-His-Thr-Gln-Ser-Pro-Leu-Phe-Val-Gly-Lys-Val-Val-Asp-Pro-Thr-His (SEQ ID NO: 4) corresponding to residues 378-412 of Mus Musculus alpha-1-antitrypsin (serpin a1c) are highly effective in eliminating neurological damages in animal models of multiple sclerosis.

While the principles of the present invention are exemplified herein below with polypeptides derived from mouse alpha-1 antitrypsin useful in treating inflammatory and autoimmune diseases in animal models or used for treatment of sepsis and asthma in animal models, the present invention encompasses homologous polypeptides derived from human alpha-1 antitrypsin, particularly useful for treating inflammatory and autoimmune diseases in humans.

According to a first aspect, the present invention provides a composition comprising an isolated polypeptide, wherein said composition is pharmaceutically acceptable, said polypeptide diminishes or abrogates an inflammatory response in a subject and said polypeptide shares at least 95% identity with a polypeptide consisting of an amino acid sequence selected from the group consisting of SEQ ID NO:1, SEQ ID NO:2, SEQ ID NO: 3 and SEQ ID NO: 4

In some aspects, the isolated polypeptide comprises a amino acid sequence sharing at least 95% identity with that set forth in SEQ ID NO:1, or a fragment thereof, or in some embodiments, the amino acid sequence shares at least 97% identity with that set forth in SEQ ID NO: 1, or in some embodiments, the amino acid sequence shares at least 99% identity with that set forth in SEQ ID NO: 1. In some embodiments, the amino acid sequence consists of that set forth in SEQ ID NO: 1.

In some embodiments, the polypeptide comprises an amino acid sequence sharing at least 97% identity with that set forth in SEQ ID NO:2 or a fragment thereof, or in some embodiments, the amino acid sequence shares at least 99% identity with that set forth in SEQ ID NO:2. In some embodiments, the amino acid sequence consists of that set forth in SEQ ID NO:2.

In some embodiments, the polypeptide comprises an amino acid sequence sharing at least 97% identity with that set forth in SEQ ID NO: 3, or in some embodiments, the amino acid sequence shares at least 99% identity with that set forth in SEQ ID NO: 3. In some embodiments, the amino acid sequence consists of that set forth in SEQ ID NO: 3. In some embodiments, the compositions and methods of use envision incorporating an isolated polypeptide, which is a further fragment of the polypeptides described hereinabove.

In some embodiments, the polypeptide comprises an amino acid sequence sharing at least 97% identity with that set forth in SEQ ID NO: 4, or in some embodiments, the amino acid sequence shares at least 99% identity with that set forth in SEQ ID NO: 4. In some embodiments, the amino acid sequence consists of that set forth in SEQ ID NO: 4. In some embodiments, the compositions and methods of use envision incorporating an isolated polypeptide, which is a further fragment of the polypeptides described hereinabove.

The polypeptides of the present invention and incorporated in the compositions of this invention and for use in accordance with the methods of this invention corresponding to residues 378-413 of alpha-1 antitrypsin can have at least one amino acid deletion, or, in some embodiments, at least 2, or in some embodiments, at least 3, or in some embodiments, at least 4, or in some embodiments, at least 5, or in some embodiments, at least 6, and up to 15 amino acid residue deletion at the amino terminus, or at the carboxyl terminus, or both so long as the peptide retains anti-inflammatory activity.

According to another aspect, the present invention provides a pharmaceutical composition comprising as an active agent an isolated polypeptide as herein described, which in some embodiments, comprises an amino acid sequence, sharing at least 95%, or in some embodiments, at least 97%, or in some embodiments, at least 99%, with that set forth in SEQ ID NO: 1, or in some embodiments as set forth in SEQ ID NO:1, or a biologically active analog, derivative, or fragment thereof; and a pharmaceutically acceptable carrier.

In some embodiments, the pharmaceutical composition comprises as an active agent, an isolated peptide comprises an amino acid sequence, sharing at least 95%, or in some embodiments, at least 97%, or in some embodiments, at least 99%, with that set forth in any one of SEQ ID NOs:2 to SEQ ID NO:4, or as set forth in any one of SEQ ID NOs:2 to SEQ ID NO:4, or a biologically active analog, derivative, or fragment thereof; and a pharmaceutically acceptable carrier.

According to some embodiments, the pharmaceutical composition is formulated in a form selected from the group consisting of a solution, suspension, emulsion, powder, cream, lotion, gel, foam, spray, or aerosol.

According to a further aspect, the present invention provides a method for treating inflammation, for example, inflammation and/or inflammation caused by severe infections, the method comprising administering to a subject in need of such treatment a therapeutically effective amount of a an isolated peptide comprising the amino acid sequence as set forth in SEQ ID NO:1, SEQ ID NO: 2, SEQ ID NO: 3 or SEQ ID NO: 4, or a biologically active analog, derivative or fragment thereof, or a pharmaceutical composition comprising a polypeptide as herein described as an active agent and a pharmaceutically acceptable carrier. Preferably, the subject is a human.

According to some embodiments, the pharmaceutical composition useful for treating inflammation comprises as an active agent an isolated polypeptide as set forth in any one of SEQ ID NOs:1 to SEQ ID NO:4, or a combination thereof.

According to some embodiments, the route of administering the pharmaceutical composition is selected from the group consisting of intravenous, subcutaneous, intramuscular, intraperitoneal, oral, nasal, transnasal, intranasal, sublingual, aerosol, rectal, vaginal, and/or directly or adjacent to a damaged tissue. According to a certain embodiment, the route of administering the pharmaceutical composition is by intraperitoneal administration.

Due to their anti-inflammatory and immuno-modulating properties, the pharmaceutical compositions of the present invention are useful for treating a diverse group of indications having an inflammatory or autoimmune mechanism involved in their etiology or pathogenesis. According to some embodiments, the disease or condition is selected from the group consisting of inflammatory diseases, autoimmune diseases, degenerative neurological diseases, degenerative muscle diseases, wounds, hypersensitivity, infectious diseases, diseases associated with graft transplantation, allergic diseases, musculo-skeletal inflammations, and sepsis According to additional embodiments, the inflammatory or autoimmune disease is selected from the group consisting of systemic lupus erythematosus (SLE), multiple sclerosis, arthritis including rheumatoid arthritis, inflammatory bowel disease (Crohn's disease), asthma, allergy, chronic bronchitis, sepsis, and psoriasis. According to certain exemplary embodiments, the disease to be treated is systemic lupus erythematosus (SLE), multiple sclerosis (MS) or psoriasis.

According to additional embodiments, the degenerative neurological disease is selected from the group consisting of amyotrophic lateral sclerosis, Parkinson's disease, and Alzheimer's disease.

According to a still further aspect, the present invention provides a method for protecting against or treating a T- or B-cell mediated disease comprising administering to the subject in need of such treatment a therapeutically effective amount of a pharmaceutical composition according to the principles of the present invention, and a pharmaceutically acceptable carrier. According to some embodiments, the pharmaceutical composition to be administered for protecting against or treating a T- or B-cell mediated disease in a subject comprises a peptide of SEQ ID NO:1. Preferably, the subject is human.

According to some embodiments, T- or B-cell mediated disease that can be treated by a pharmaceutical composition of the invention is selected from the group consisting of psoriasis; allergy; T or B cell lymphomas and other malignancies; graft versus host disease; bronchitis; asthma; allergy; autoimmunity; sarcoidosis; bone marrow depression; bone marrow stimulation; depression or other mood or psychotic disorders; sepsis; myasthenia gravis (MG); Parkinson's disease; skin disorders and irritation; arthritis; multiple sclerosis; neurodegenerative disorders (amyotrophic lateral sclerosis, chorea, Alzheimer disease); atherosclerosis; fibrosis; pain; chronic or acute inflammation. The polypeptides and pharmaceutical compositions of the present invention can be used in combination therapy with standard medicaments for the diseases listed herein above.

According to a further aspect, the present invention provides use of the polypeptides of the invention in the preparation of a medicament for treating a disease or condition attributable to inflammatory processes. A specific example of such a diseases is sepsis It should be appreciated that alpha-1-antitrypsin or any known fragment thereof are excluded from the polypeptides of the present invention and from the compositions of the present inventions, per se, but are disclosed and claimed for the novel uses discloses herein.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 6A shows the effect of UBE on cumulative anti-dsDNA antibodies in blood samples of MRL/lpr mice having spontaneous lupus-like syndrome. FIGS. 6B, 6C, 6D and 6E show specific IgM, IgG1, IgG2a and IgG2b responses, respectively.

FIG. 8A and FIG. 8B show FACS analysis results of control and UBE-treated peripheral lymph node cells in terms of the number of double negative CD4− CD8− cells and FIG. 8E plots the cumulative results. FIG. 8C and FIG. 8D show FACS analysis results of control and UBE-treated peripheral lymph node cells in terms of the number of double negative CD4− CD8− cells and FIG. 8F plots the cumulative results. FIG. 8G and FIG. 8H show FACS analysis results of control and UBE-treated peripheral lymph node cells in terms of the number of B220+ cells and FIG. 8K plots the cumulative results. Similarly, FIG. 8I and FIG. 8J show FACS analysis results of control and UBE-treated spleen cells in terms of the number of B220+ cells and FIG. 8L plots the cumulative results.

FIG. 10 shows the effect of UBE on proteinuria in MRL/lpr mice having spontaneous lupus-like syndrome at advanced stage of the disease.

FIG. 14A and FIG. 14B show FACS analysis results of control and UBE-treated spleen cells, respectively, in terms of the number of double negative CD4− CD8− cells and FIG. 14C plots the cumulative results.

FIG. 14D and FIG. 14E show FACS analysis results of control and UBE-treated isolated blood cells, respectively, in terms of the number of double negative CD4− CD8− cells and FIG. 14F plots the cumulative results.

FIG. 16 shows the effect of UBE or UBE1 on joint swelling in arthritic mice.

FIG. 20A shows that treatment with both 1.0 µg/kg and 10 µg/kg UBE provided for survival of approximately 50% of the mice treated, whereas only 20% of controls survived to 50 hours post LPS injection. FIG. 20B shows that 0.1 and 1.0 µg/kg UBE treatment reduced mortality by 33%.

FIG. 22A-FIG. 22G plot CD4 cell cytokine production in cells isolated from healthy human donors+/−UBE-treatment (100 ng/ml), following their activation with human anti CD3 antibodies (1 ug/ml) and human anti CD28 antibodies (1 ug/ml). The cytokines evaluated included IL6 (FIG. 22A), IL17A (FIG. 22B), IL21 (FIG. 22C), IL22 (FIG. 22D), IL23 (FIG. 22E), IL31 (FIG. 22F) and IFNγ (FIG. 22G). IL22, IL23 and IL31 were significantly reduced in UBE treated cells, as compared to controls and an overall trend in reduced inflammatory mediators was evident from these results, as well. *p<0.02, **p<0.006 using students t-test for comparison between UBE-treated and control cells.

DETAILED DESCRIPTION OF THE INVENTION

Figure 1:
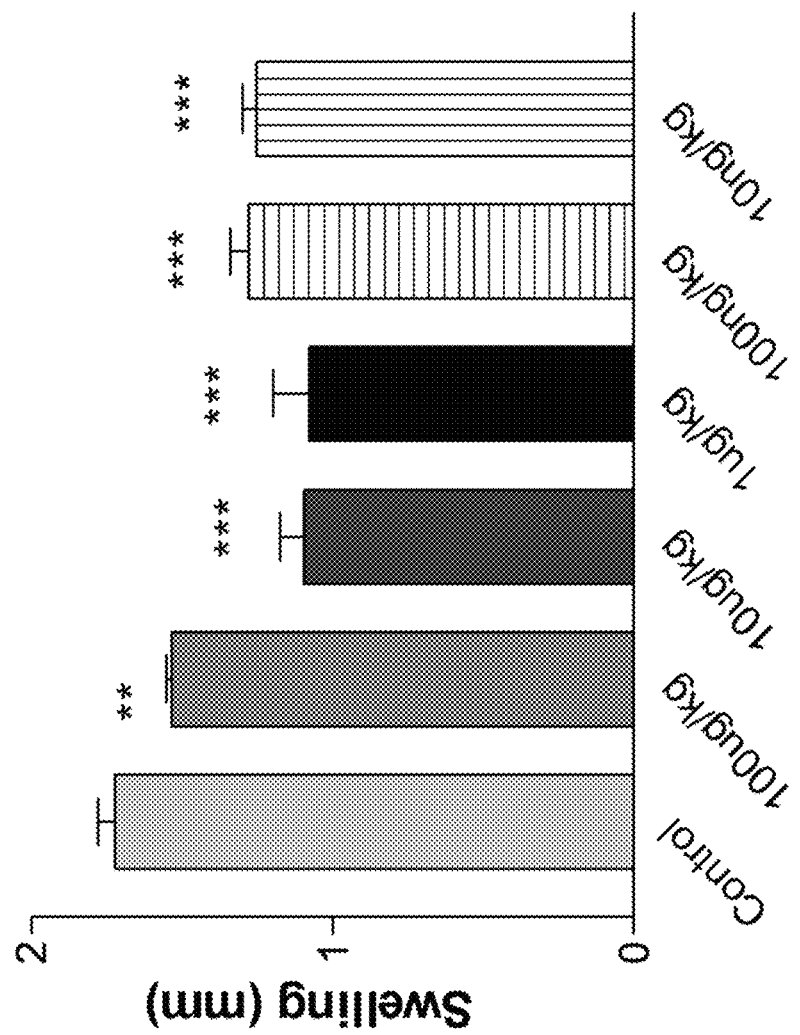
FIG. 1 shows the effect of UBE on Carrageenan-induced hind paw swelling.

The present invention provides isolated polypeptides derived from the amino acid sequence at positions 378 to 413 of *Mus musculus* Alpha 1-antitrypsin (serine protease inhibitor, Glade A, member 1c), analogs, derivatives, and fragments thereof. The present invention provides pharmaceutical compositions comprising same and uses thereof for treating conditions attributable to inflammatory processes.

Particularly, the present invention provides a composition comprising an isolated polypeptide termed UBE1 having the sequence YSMPPIVRFDHPFLFIIFEEHTQSPLFVGKVVDPTHK as set forth in SEQ ID NO:1 derived from amino acid residues 377 to 413 of *Mus Musculus* Alpha 1-antitrypsin. The present invention also provides a composition comprising an isolated polypeptide termed UBE having the sequence SMPPIVRFDHPFLFIIFEEHTQSPLFVGKVVDPTHK as set forth in SEQ ID NO:2 derived from amino acid residues 378 to 413 of *Mus musculus* Alpha 1-antitrypsin (serine protease inhibitor, Glade A, member 1c). The present invention further provides a composition comprising an isolated peptide termed UBE-N having the sequence MPPIVRFDHPFLFIIFEEHTQSPLFVGKVVDPTHK as set forth in SEQ ID NO:3 derived from amino acid residues 379 to 413 of *Mus musculus* Alpha 1-antitrypsin. The present invention further provides a composition comprising an isolated peptide termed UBE-C having the sequence SMPPIVRFDHPFLFIIFEEHTQSPLFVGKVVDPTH as set forth in SEQ ID NO:4 derived from amino acid residues 378 to 412 of *Mus musculus* Alpha 1-antitrypsin. Furthermore, the polypeptides as noted herein are nature-based products, which differ from products of nature. In some aspects, the polypeptides as described herein differ structurally from the natural product and in some aspects, the polypeptides as described herein differ functionally from the natural product, and in some aspects, the polypeptides as described herein differ in other ways from the natural product, such that the polypeptides of this invention are markedly different from natural products.

The polypeptides of the present invention and compositions as herein described exert anti-inflammatory and/or anti-autoimmune activity, and therefore useful for treating or protecting a subject against inflammatory conditions and/or diseases associated with autoimmune activity.

As exemplified herein below, administration of the peptide UBE and its derivatives resulted in pharmacological effects on animal models of SLE, multiple sclerosis (MS), arthritis, sepsis and asthma. The polypeptides of the present invention protected against renal dysfunction in mice having SLE as measured by proteinuria and hematuria and reduced serum anti dsDNA antibodies in these mice, hence improved animal survival. The polypeptides of the present invention ameliorated neurological symptoms in an animal model of multiple sclerosis (MS). The polypeptides of the invention improved survival of mice injected with LPS an accepted model for sepsis. The polypeptides of the present invention reduced some of the hallmarks of airway inflammation by diminishing the % eosinophil recovery in BAL in a murine experimental asthma model.

As described herein, the polypeptides of the present invention and compositions as herein described were also capable of suppressing proliferation of isolated T cells. The polypeptides of the present invention and therefore and compositions as herein described demonstrate anti-proliferative effects on cultured also on non-immune cells such as HaCaT keratinocytes. The polypeptides of the present invention and compositions as herein described are, therefore, useful for treating diseases such as inflammatory, autoimmune, and connective tissue diseases.

The term "polypeptide" as used herein refers to a linear series of natural, non-natural and/or chemically modified amino acid residues connected one to the other by peptide bonds. The amino acid residues are represented throughout the specification and claims by either one or three-letter codes, as is commonly known in the art. The term "isolated polypeptide" refers to a polypeptide which has been separated from polypeptides, proteins or other biological molecules which are present in a naturally occurring state. The term "isolated polypeptide" refers to a polypeptide which is markedly different from polypeptides, proteins or other biological molecules which are present in a naturally occurring state, as described herein.

The terms "analog" and "derivative" refer to a polypeptide comprising at least one altered amino acid residue by an amino acid substitution, addition, deletion, or chemical modification, as compared with the native peptide. Polypeptide derivatives particularly include amino acid substitutions and/or additions with naturally occurring amino acid residues, and chemical modifications such as, for example, enzymatic modifications, typically present in nature. Polypeptide analogs particularly include amino acid substitutions and/or additions with non-natural amino acid residues, and chemical modifications which do not occur in nature.

Thus, the present invention encompasses polypeptide derivatives and analogs of the polypeptides of the present invention. According to the principles of the present invention the polypeptides of the present invention do not include the intact alpha-1 antitrypsin protein or any known fragments thereto.

The term "the polypeptides of the present invention" refers to the polypeptides disclosed herein as UBE (SEQ ID NO:2), UBE1 (SEQ ID NO:1), UBE-N(SEQ ID NO:3), UBE-C (SEQ ID NO:4), analogs, derivatives and fragments thereof.

By using "amino acid substitutions", it is meant that functionally equivalent amino acid residues are substituted for residues within the sequence resulting in a silent change. The term "functionally equivalent" means, for example, a group of amino acids having similar polarity, similar charge, or similar hydrophobicity. For example, one or more amino acid residues within the sequence can be substituted by another amino acid of a similar polarity, which acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are known as conservative substitutions. Additionally, a non-conservative substitution can be made in an amino acid that does not contribute to the biological activity of the polypeptide. Such non-conservative substitutions are also encompassed within the term "amino acid substitution", as used herein. It will be appreciated that the present invention further encompasses the polypeptides of the present invention, derivatives or analogs, wherein at least one amino acid is substituted by another amino acid to produce a polypeptide derivative or analog having increased stability or higher half life as compared to the polypeptides of the present invention.

The present invention encompasses polypeptides of which at least one amino acid has been chemically modified. Chemical modifications of amino acid residues include, but are not limited to, amidation, methylation, acetylation, glycosylation, oxidation, reduction, myristylation, sulfation, acylation, ADP-ribosylation, cyclization, hydroxylation, iodination, derivatization by protecting/blocking groups, or any other derivatization method known in the art. Such alterations, which do not destroy, but may improve the biological activity of the polypeptides of the present invention, can occur anywhere along the sequence of the polypeptide, including at the peptide backbone, the amino acid side-chains, and at the amino or carboxyl termini.

The term "fragment" as used herein refers to a portion of a polypeptide, polypeptide derivative or polypeptide analog having an anti-inflammatory and/or anti-inflammatory activity.

The present invention encompasses polypeptide hydrates. The term "hydrate" includes, but is not limited to, hemihydrate, monohydrate, dihydrate, trihydrate, and the like.

The polypeptides of the present invention, analogs, derivatives and fragments thereof can be produced by various methods known in the art, including recombinant production or synthetic production. Recombinant production can be achieved by the use of an isolated polynucleotide encoding the polypeptides of the present invention, or a fragment, derivative or analog thereof, the isolated polynucleotide operably linked to a promoter for the expression of the polynucleotide. Optionally, a signal polypeptide and a regulator of the promoter are added. The construct comprising the polynucleotide encoding the polypeptides of the present invention, or a fragment, derivative or analog thereof, the promoter, and optionally the regulator can be placed in a vector, such as a plasmid, virus or phage vector. The vector can be used to transfect or transform a host cell, e.g., a bacterial, yeast, insect, or mammalian cell. The vector can also be introduced into a transgenic animal such as, for example, a transgenic mouse.

Alternatively, the polypeptide can be produced synthetically. Synthetic production of polypeptides is well known in the art. The polypeptides of the present invention, derivatives, analogs and/or fragments thereof can be synthesized using standard direct polypeptide synthesis (see, for example, Bodanszky, 1984, Principles of Polypeptide Synthesis, Springer-Verlag, Heidelberg), such as via solid-phase synthesis (see, for example, Merrifield, 1963, J. Am. Chem. Soc. 85:2149-2154, the contents of which are hereby incorporated by reference in their entirety). Examples of solid phase polypeptide synthesis methods include, but are not limited to, the BOC method, which utilizes tert-butyloxycarbonyl as the α-amino protecting group, and the FMOC method, which utilizes 9-fluorenylmethyloxcarbonyl to protect the α-amino of the amino acid residues, both methods are well-known by those of skill in the art.

Alternatively, the polypeptide derivatives, analogs, and fragments of the present invention can be synthesized using standard solution methods (see, for example, Bodanszky, M., Principles of Peptide Synthesis, Springer-Verlag, 1984, the content of which is hereby incorporated by reference in its entirety).

The polypeptide derivatives, analogs, and fragments according to the principles of the present invention can also include side chain bond modifications, including but not limited to —CH$_2$—NH—, —CH$_2$—S—, —CH$_2$—S=O, O=C—NH—, —CH$_2$—O—, —CH$_2$—CH$_2$—, S=C—NH—, and —CH=CH—, and backbone modifications such as modified polypeptide bonds. Polypeptide bonds (—CO—NH—) within the polypeptide can be substituted, for example, by N-methylated bonds (—N(CH3)-CO—); ester bonds (—C(R)H—C—O—O—C(R)H—N); ketomethylene bonds (—CO—CH2-); α-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefinic double bonds (—CH=CH—); and polypeptide derivatives (—N(R)—CH2-CO—), wherein R is the "normal" side chain, naturally presented on the carbon atom. These modifications can occur at one or more of the bonds along the polypeptide chain and even at several (e.g., 2-3) at the same time.

The present invention also encompasses polypeptide derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, amides, methyl and ethyl esters or other types of esters or hydrazides. The imidazole nitrogen of histidine can be derivatized to form N-imbenzylhistidine.

Also included are those polypeptide derivatives, which contain one or more naturally occurring amino acid derivatives of the twenty standard amino acid residues. For example: 4-hydroxyproline can be substituted for proline; 5-hydroxylysine can be substituted for lysine; 3-methylhistidine can be substituted for histidine; homoserine can be substituted or serine; and ornithine can be substituted for lysine. The polypeptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the polypeptide analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like.

The invention further includes the polypeptides of the present invention analogs, which can contain one or more D-isomer forms of the amino acids. Production of retro-inverso D-amino acid polypeptides where at least one amino acid, and perhaps all amino acids, is D-amino acids is well known in the art. When all of the amino acids in the polypeptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein.

Included within the scope of the invention are polypeptide conjugates comprising the polypeptides of the present invention derivatives, analogs, or fragments thereof joined at their amino or carboxy-terminus or at one of the side chains via a polypeptide bond to an amino acid sequence of a different protein. Additionally or alternatively, the polypeptides of the present invention, derivatives, analogs, or fragments thereof can be joined to another moiety such as, for example, a fatty acid, a sugar moiety, arginine residues, and any known moiety that facilitate membrane or cell penetration. Conjugates comprising polypeptides of the invention and a protein can be made by protein synthesis, e. g., by use of a peptide synthesizer, or by ligating the appropriate nucleic acid sequences encoding the desired amino acid sequences to each other by methods known in the art, in the proper coding frame, and expressing the conjugate by methods commonly known in the art.

The person skilled in the art would have no problem in determining which of the polypeptide analogs, derivatives or fragments falls under the scope of the invention. A polypeptide derivative, analog, or fragment can be prepared and tested in one of the assays disclosed herein below: assays for anti-inflammatory activity (see the assay of hind paw swelling in Example 1), assay for evaluating neurological damage in mice having assays for proteinuria, microhematuria, anti dsDNA antibodies, and kidney pathological score in mice having systemic lupus erythematosus (see Example 4,). A polypeptide derivative, analog, or fragment which is active in one of these assays or in any assay aimed at evaluating an anti-inflammatory activity, as known in the art (see, for example, WO 2005/090387, the content of which is incorporated by reference as if fully set forth herein) falls under the scope of the invention.

According to another aspect, the present invention provides an isolated polynucleotide sequence encoding the polypeptides of the present invention, or a fragment, derivative, analog, or a conjugate thereof, the polypeptides of the present invention, fragment, derivative, analog, or conjugate thereof have anti-inflammatory activity and/or T cell inhibitory activity.

The term "polynucleotide" means a polymer of deoxyribonucleic acid (DNA), ribonucleic acid (RNA) or a combination thereof, which can be derived from any source, can be single- or double-stranded, and can optionally contain synthetic, non-natural, or altered nucleotides, which are capable of being incorporated into DNA or RNA polymers.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs.

The term also applies to polynucleotides, which have been substantially purified from other components, which naturally accompany the polynucleotide in the cell, e.g., RNA or DNA or proteins. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence, and RNA such as mRNA.

The term "encoding" refers to the inherent property of specific sequences of nucleotides in an isolated polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a polypeptide or protein if transcription and translation of mRNA corresponding to that gene produces the polypeptide or protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the polypeptide or protein or other product of that gene or cDNA.

One who is skilled in the art will appreciate that more than one polynucleotide may encode any given polypeptide or protein in view of the degeneracy of the genetic code and the allowance of exceptions to classical base pairing in the third position of the codon, as given by the so-called "Wobble rules." It is intended that the present invention encompass polynucleotides that encode the polypeptides of the present invention as well as any derivative, analog, and fragment thereof.

A polynucleotide of the present invention can be expressed as a secreted polypeptide where the polypeptides of the present invention, a derivative, analog or fragment thereof is isolated from the medium in which the host cell containing the polynucleotide is grown, or the polynucleotide can be expressed as an intracellular polypeptide by deleting the leader or other polypeptides, in which case the polypeptides of the present invention, derivative, analog or fragment thereof is isolated from the host cells. The polypeptides of the present invention, derivative, analog or fragment thereof so isolated is then purified by standard protein purification methods known in the art.

The polypeptides of the present invention, analogs, derivatives, or fragments thereof can also be provided to the tissue of interest by transferring an expression vector comprising an isolated polynucleotide encoding the polypeptides of the present invention, an analog, derivative, or fragment thereof to cells associated with the tissue of interest. The cells produce the polypeptide such that it is suitably provided to the cells within the tissue to exert a biological activity such as, for example, to reduce or inhibit inflammatory processes within the tissue of interest.

The expression vector according to the principles of the present invention further comprises a promoter. In the context of the present invention, the promoter must be able to drive the expression of the polypeptide within the cells. Many viral promoters are appropriate for use in such an expression vector (e.g., retroviral ITRs, LTRs, immediate early viral promoters (IEp) (such as herpes virus IEp (e.g., ICP4-IEp and ICP0-IEp) and cytomegalovirus (CMV) IEp), and other viral promoters (e.g., late viral promoters, latency-active promoters (LAPs), Rous Sarcoma Virus (RSV) promoters, and Murine Leukemia Virus (MLV) promoters). Other suitable promoters are eukaryotic promoters, which contain enhancer sequences (e.g., the rabbit β-globin regulatory elements), constitutively active promoters (e.g., the β-actin promoter, etc.), signal and/or tissue specific promoters (e.g., inducible and/or repressible promoters, such as a promoter responsive to TNF or RU486, the metallothionine promoter, etc.), and tumor-specific promoters.

Within the expression vector, the polynucleotide encoding the polypeptides of the present invention, an analog, derivative or fragment thereof and the promoter are operably linked such that the promoter is able to drive the expression of the polynucleotide. As long as this operable linkage is maintained, the expression vector can include more than one gene, such as multiple genes separated by internal ribosome entry sites (IRES). Furthermore, the expression vector can optionally include other elements, such as splice sites, polyadenylation sequences, transcriptional regulatory elements (e.g., enhancers, silencers, etc.), or other sequences.

The expression vectors are introduced into the cells in a manner such that they are capable of expressing the isolated polynucleotide encoding the polypeptides of the present invention, a fragment, derivative or analog thereof contained therein. Any suitable vector can be so employed, many of which are known in the art. Examples of such vectors include naked DNA vectors (such as oligonucleotides or plasmids), viral vectors such as adeno-associated viral vectors (Berns et al., 1995, Ann. N.Y. Acad. Sci. 772:95-104, the contents of which are hereby incorporated by reference in their entirety), adenoviral vectors, herpes virus vectors (Fink et al., 1996, Ann. Rev. Neurosci. 19:265-287), packaged amplicons (Federoff et al., 1992, Proc. Natl. Acad. Sci. USA 89:1636-1640, the contents of which are hereby incorporated by reference in their entirety), papilloma virus vectors, picornavirus vectors, polyoma virus vectors, retroviral vectors, SV40 viral vectors, vaccinia virus vectors, and other vectors. Additionally, the vector can also include other genetic elements, such as, for example, genes encoding a selectable marker (e.g., β-gal or a marker conferring resistance to a toxin), a pharmacologically active protein, a transcription factor, or other biologically active substance.

Methods for manipulating a vector comprising an isolated polynucleotide are well known in the art (e.g., Sambrook et al., 1989, Molecular Cloning: A Laboratory Manual, 2d edition, Cold Spring Harbor Press, the contents of which are hereby incorporated by reference in their entirety) and include direct cloning, site specific recombination using recombinases, homologous recombination, and other suitable methods of constructing a recombinant vector. In this manner, an expression vector can be constructed such that it can be replicated in any desired cell, expressed in any desired cell, and can even become integrated into the genome of any desired cell.

The expression vector comprising the polynucleotide of interest is introduced into the cells by any means appropriate for the transfer of DNA into cells. Many such methods are well known in the art (e.g., Sambrook et al., supra; see also Watson et al., 1992, Recombinant DNA, Chapter 12, 2d edition, Scientific American Books, the contents of which are hereby incorporated by reference in their entirety). Thus, in the case of prokaryotic cells, vector introduction can be accomplished, for example, by electroporation, transformation, transduction, conjugation, or mobilization. For eukaryotic cells, vectors can be introduced through the use of, for example, electroporation, transfection, infection, DNA coated microprojectiles, or protoplast fusion. Examples of eukaryotic cells into which the expression vector can be introduced include, but are not limited to, ovum, stem cells, blastocytes, and the like.

Cells, into which the polynucleotide has been transferred under the control of an inducible promoter if necessary, can be used as transient transformants. Such cells themselves may then be transferred into a subject for therapeutic benefit therein. Thus, the cells can be transferred to a site in the subject such that the polypeptide of the invention is expressed therein and secreted therefrom and thus reduces or inhibits, for example, inflammatory processes so that the clinical condition of the subject is improved. Alternatively, particularly in the case of cells to which the vector has been added in vitro, the cells can first be subjected to several rounds of clonal selection (facilitated usually by the use of a selectable marker sequence in the vector) to select for stable transformants. Such stable transformants are then transferred to a subject, preferably a human, for therapeutic benefit therein.

Within the cells, the polynucleotide encoding the polypeptides of the present invention, an analog, derivative or fragment thereof is expressed, and optionally is secreted. Successful expression of the polynucleotide can be assessed using standard molecular biology techniques (e.g., Northern hybridization, Western blotting, immunoprecipitation, enzyme immunoassay, etc.).

The polypeptides of the present invention, analogs, derivatives or fragments thereof produced by recombinant techniques can be purified so that the polypeptides will be substantially pure when administered to a subject. The term "substantially pure" refers to a compound, e.g., a polypeptide, which has been separated from components, which naturally accompany it. Typically, a polypeptide is substantially pure when at least 50%, preferably at least 75%, more preferably at least 90%, and most preferably at least 99% of the total material (by volume, by wet or dry weight, or by mole percent or mole fraction) in a sample is the polypeptide of interest. Purity can be measured by any appropriate method, e.g., in the case of polypeptides by HPLC analysis.

The present invention encompasses transgenic animals comprising an isolated polynucleotide encoding the polypeptides of the invention.

With regard to the polypeptides and/or polynucleotides as herein described, it will be appreciated that such polypeptides and/or polynucleotides encoding the same, which are considered to be encompassed by the invention include polypeptides and/or polynucleotides encoding the same, comprising a sequence homologous to what is set forth in SEQ ID NOs: 1-4. "Identity" or "homology" with respect to polypeptides/polynucleotides and their functional derivatives refers, inter alia, to the percentage of amino acid residues in the candidate sequence that are identical with the residues of a corresponding reference, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known in the art.

In some embodiments, the polypeptides/polynucleotides and their functional derivatives will share at least 80%, or in some embodiments, at least 85%, or in some embodiments, at least 87%, or in some embodiments, at least 90%, or in some embodiments, at least 92%, or in some embodiments, at least 95%, or in some embodiments, at least 77%, or in some embodiments, at least 99% identity with the reference sequence.

It is to be appreciated that the polypeptides of the present invention and incorporated in the compositions of this invention and for use in accordance with the methods of this invention consist of at least 6 amino acid residues, or in some embodiments, at least 7 amino acid residues, or in some embodiments, at least 8, or in some embodiments, at least 9, or in some embodiments, at least 10, or in some embodiments, at least 11, or in some embodiments, at least 12, or in some embodiments, at least 13, or in some embodiments, at least 14, or in some embodiments, at least 15, or in some embodiments, at least 16, or in some embodiments, at least 17, or in some embodiments, at least 18, or in some embodiments, at least 19, or in some embodiments, at least 20, or in some embodiments, at least 25, or in some embodiments, at least 30, or in some embodiments, at least 35, or in some embodiments, at least 40, or in some embodiments, at least 45, or in some embodiments, at least up to 50 amino acid residues.

The polypeptides of this invention may include amino acid sequence variants. The term "amino acid sequence variant" refers to molecules with some differences in their amino acid sequences as compared to a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native sequence. Immediately adjacent to an amino acid means connected to either the .alpha.-carboxy or .alpha.-amino functional group of the amino acid.

Deletional variants are those with one or more amino acids in the native amino acid sequence removed. Ordinarily, deletional variants will have one or two amino acids deleted in a particular region of the molecule.

A "functional derivative" of the polypeptides of this invention include compounds having a qualitative biological activity in common with the native polypeptide. "Functional derivatives" include, but are not limited to, fragments of native polypeptides from any animal species (including humans), and derivatives of native (human and non-human) polypeptides and their fragments, provided that they have a biological activity in common with a respective native polypeptide. The polypeptides of this invention include fragments of the polypeptides having a sequence as set forth in SEQ ID NO: 1. "Fragments" comprise regions within the sequence of a full reference polypeptide. The term "derivative" is used to define amino acid sequence and glycosylation variants, and covalent modifications of a polypeptide, whereas the term "variant" refers to amino acid sequence and glycosylation variants within this definition.

Pharmaceutical Compositions and Administration Routes

The present invention provides pharmaceutical compositions comprising as an active agent a therapeutically effective amount of a source of the polypeptides of the current invention, and a pharmaceutically acceptable carrier.

The source of the polypeptides of the current invention refers herein to UBE, UBE1, UBE-C and UBE-N polypeptides, derivatives, analogs or fragments thereof, to an isolated polynucleotide encoding the polypeptides of the current invention, a derivative, analog or fragment thereof, to an expression vector comprising an isolated polynucleotide encoding the polypeptides of the current invention, a derivative, analog or fragment thereof, or to cells transfected with the expression vector as described herein above.

The pharmaceutical compositions of the invention can be formulated in the form of a pharmaceutically acceptable salt of the polypeptides of the present invention or their analogs, derivatives or fragments thereof. Pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

The term "pharmaceutically acceptable" means suitable for administration to a subject, e.g., a human. For example, the term "pharmaceutically acceptable" can mean approved by a regulatory agency of the Federal or a state government or listed in the U. S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned.

The pharmaceutical compositions of this invention may further comprise additional stabilizing agents. In some aspects, the composition may include disodium EDTA, which in turn may serve to extend the shelf life, or in some embodiments, increase polypeptide stability, or in some embodiments, sustain polypeptide potency, and other benefits as will be appreciated by the skilled artisan. In some aspects, the composition may include one or more metal chelators.

The compositions can take the form of solutions, suspensions, emulsions, tablets, pills, capsules, powders, gels, creams, ointments, foams, pastes, sustained-release formulations and the like. The compositions can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of a source of the polypeptides of the current invention, preferably in a substantially purified form, together with a suitable amount of carrier so as to provide the form for proper administration to the subject.

The amount of a source of the polypeptides of the current invention, which will be effective in the treatment of a particular disorder or condition will depend on the nature of the disorder or condition and on the particular polypeptide source, and can be determined by standard clinical techniques known to a person skilled in the art. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

Depending on the location of the tissue of interest, a source of the polypeptides of the current invention can be supplied in any manner suitable for the provision of the polypeptide to cells within the tissue of interest. Thus, for example, a composition containing a source of the polypeptides of the current invention (i.e., a UBE polypeptide, derivative, analog or fragment thereof, or an isolated polynucleotide encoding the UBE polypeptide, a derivative, analog or fragment thereof, or an expression vector comprising an isolated polynucleotide encoding the UBE polypeptide, a derivative, analog or fragment thereof, or cells transfected with the expression vector as described herein above) can be introduced, for example, into the systemic circulation, which will distribute the source of the polypeptides to the tissue of interest. Alternatively, a composition containing a source of the polypeptides of the current invention can be applied topically to the tissue of interest (e.g., injected, or pumped as a continuous infusion, or as a bolus within a tissue, applied to all or a portion of the surface of the skin, etc.).

The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of polypeptides administered by other routes can be lower than when administered via parenteral injection, by using appropriate formulations it is envisaged that it will be possible to administer the compositions of the invention via oral, transdermal, rectal, vaginal, topical, nasal, transnasal, intranasal, sublingual, inhalation and ocular modes of treatment. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

It may be desirable to administer the pharmaceutical composition of the invention locally to the area in need of treatment; this can be achieved by, for example, and not by way of limitation, local infusion, topical application, by injection, by means of a catheter, by means of a suppository, or by means of an implant, said implant being of a porous, non-porous, or gelatinous material. According to some preferred embodiments, administration can be by direct injection e.g., via a syringe, at the site of a damaged tissue.

For topical application, the polypeptides of the current invention, or a derivative, analog or fragment thereof can be combined with a pharmaceutically acceptable carrier so that an effective dosage is delivered, based on the desired activity. According to an exemplary embodiment, the polypeptide of the invention is applied to the skin for treatment of diseases such as psoriasis. The carrier can be in the form of, for example, and not by way of limitation, an ointment, cream, gel, paste, foam, aerosol, suppository, pad or gelled stick.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to the ingredients of the above type, a liquid carrier such as fatty oil. In addition, dosage unit forms can contain various other materials which modify the physical form of the dosage unit, for example, coatings of sugar, shellac, or other enteric agents. The tablets of the invention can further be film coated.

The polypeptides of the current invention derivatives, analogs or fragments thereof can be delivered in a controlled release system. Thus, an infusion pump can be used to administer the polypeptide such as the one that is used, for example, for delivering insulin or chemotherapy to specific organs or tumors. In one embodiment, the polypeptide of the invention is administered in combination with a biodegradable, biocompatible polymeric implant, which releases the polypeptide over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

In some aspects, the polypeptides comprise a nanoparticle formulation, by methods well known in the art, for example, as described in U.S. Pat. No. 8,404,281, United States Patent Application 20140187424, each of which is hereby incorporated by reference in its entirety. Similarly, microemulsion formulations comprising the polypeptides as described herein are contemplated, the methods of preparation of which are well known, for example, as described in WIPO Patent Application WO/1994/008605, or U.S. Pat. No. 8,741,836, each of which is hereby incorporated by reference in its entirety.

In yet another embodiment, the compositions of the present invention can be placed on a stent.

In some aspects, the polypeptides of this invention exhibit excellent potency, even when present in surprisingly low dosages. In some embodiments, the dosage may range from 0.001 micrograms-5 mg per kilogram weight of a subject. In some embodiments, the dosage may range from 0.01 micrograms-5 mg per kilogram weight of a subject. In some embodiments, the dosage may range from 0.01 micrograms-1 micrograms per kilogram weight of a subject and in some embodiments, the dosage may range from 0.05 micrograms-3 micrograms per kilogram weight of a subject. In some embodiments, the dosage may range from 0.1 micrograms-10 micrograms per kilogram weight of a subject and in some embodiments, the dosage may range from 0.5 micrograms-30 micrograms per kilogram weight of a subject. In some embodiments, the dosage may range from 0.3 micrograms-40 micrograms per kilogram weight of a subject and in some embodiments, the dosage may range from 1 microgram-100 micrograms per kilogram weight of a subject. In some embodiments, the dosage may range from 10 micrograms-500 micrograms per kilogram weight of a subject and in some embodiments, the dosage may range from 30 micrograms-30 mg per kg weight of a subject. In some embodiments, the dosage may range from 0.1 mg/kg-1 mg/kg weight of a subject and in some embodiments, the dosage may range from 1 mg/kg-50 mg/kg weight of a subject.

Uses of UBE Polypeptides

The present invention provides a method for preventing or treating diseases or disorders attributable to inflammatory processes in a subject. The present invention also provides a method for treating a disease or condition attributable to autoimmune processes in a subject. The present invention further provides a method for treating T- or B-cell mediated disease in a subject.

The present invention provides for a method for treating inflammation in a subject in need thereof, said method comprising administering to said subject a therapeutically effective amount of a polypeptide as herein described.

In some embodiments, this invention provides for the use of an isolated polypeptide as herein described, or a fragment thereof, in the preparation of a medicament for use in treating inflammation in a subject.

In some embodiments, the inflammation is associated with an autoimmune disease, a wound, hypersensitivity, a degenerative neurological disease, a degenerative muscle disease, an infectious disease, a graft transplantation, graft versus host disease, an allergy, a musculo-skeletal condition, or sepsis. In some embodiments, the inflammation is associated with systemic lupus erythematosus (SLE), multiple sclerosis, arthritis, asthma, allergy, inflammatory bowel disease, Crohn's disease, or psoriasis. In some embodiments the subject suffers from systemic lupus erythematosus (SLE) and in some embodiments, the subject suffers from multiple sclerosis. In some embodiments, the subject suffers from psoriasis.

In some embodiments, the inflammation is associated with Parkinson's disease, amyotrophic lateral sclerosis, or Alzheimer's disease. In some embodiments, the inflammation is associated with sepsis.

According to the principles of the present invention, the methods comprise the step of administering to a subject in need of such treatment a pharmaceutical composition comprising as an active agent a therapeutically effective amount of a source of the polypeptides of the current invention and a pharmaceutically acceptable carrier. The polypeptides source according to the present invention includes the UBE, UBE1, UBE-N or UBE-C polypeptides, or a derivative, analog or fragment thereof according to principles of the present invention; an isolated polynucleotide sequence encoding the polypeptide source, or a derivative, analog or fragment thereof; an expression vector comprising the isolated polynucleotide sequence encoding the polypeptide source, or a derivative, analog or fragment thereof; and a host cell transfected with the expression vector comprising the isolated polynucleotide sequence of the invention. According to a certain exemplary embodiment, the polypeptide is UBE polypeptide of SEQ ID NO: 1. According to another exemplary embodiment, the polypeptide is UBE1 polypeptide of SEQ ID NO:2. According to a yet another exemplary embodiment, the polypeptide is UBE-N polypeptide of SEQ ID NO:3. According to an additional exemplary embodiment, the polypeptide is UBE-C polypeptide of SEQ ID NO:4.

A "therapeutically effective amount" of the polypeptide source of the current invention is that amount of the polypeptide source which is sufficient to provide a beneficial effect to the subject to which the source is administered. More specifically, a therapeutically effective amount means an amount of the source effective to prevent, alleviate or ameliorate tissue damage or symptoms of a disease of the subject being treated.

As the polypeptides of the invention have proven to be particularly efficacious against inflammatory processes associated with systemic lupus erythematosus (SLE), multiple sclerosis, arthritis and sepsis. The polypeptides of the invention are therefore very useful as bona fide anti-inflammatory or immuno-modulating agents.

As anti-inflammatory or immuno-modulating agents, the polypeptides of the invention are expected to be efficacious in all diseases, disorders, or conditions that involve inflammation or inflammatory activity. Therefore, this invention relates to the protective effect of the polypeptide of the current invention against all disorders or diseases that are related to or involve inflammation.

Inflammatory diseases that can be treated by the polypeptide of the current invention include autoimmune diseases including, but not limited to, systemic lupus erythematosus (SLE), multiple sclerosis (MS), arthritis including rheumatoid arthritis, asthma, allergy, chronic bronchitis, inflammatory bowel disease (Crohn's disease), psoriasis, and sepsis.

Inflammation is also associated with chronic neurological degenerative diseases and muscle degenerative diseases. The degenerative diseases include, but are not limited to, multiple sclerosis, Alzheimer's disease, Parkinson's disease, myasthenia gravis, muscle dystrophy, and amyotrophic lateral sclerosis.

Inflammation is also associated with hypersensitivity. Hypersensitivity includes, but is not limited to, immediate hypersensitivity, antibody mediated hypersensitivity, immune complex mediated hypersensitivity, T lymphocyte mediated hypersensitivity and delayed type hypersensitivity.

Inflammation is also associated with an infectious disease. Infections-induced inflammations that can be treated with the pharmaceutical compositions of the invention include, but are not limited to those induced by viral diseases, bacterial diseases, protozoan diseases, parasitic diseases, fungal diseases, and mycoplasma diseases. Thus, the compositions comprising the polypeptide source of the invention can be used as cosmetics to eliminate skin inflammatory responses associated with infections Inflammation can also be associated with transplantation of a graft, such as, for example, in conditions of graft rejection.

Inflammation can also be associated with an allergic disease and with musculo-skeletal inflammation. The musculo-skeletal inflammation is selected from the group consisting of arthritis, muscle inflammation, myositis, a tendon inflammation, tendinitis, a ligament inflammation, a cartilage inflammation, a joint inflammation, a synovial inflammation, carpal tunnel syndrome and a bone inflammation.

The polypeptides of the invention are useful for protecting against or treating T- or B-cell mediated disease. T- or B-cell mediated diseases include, but are not limited to, psoriasis; allergy; T or B cell lymphomas and other malignancies; graft versus host disease; prevention of transplant rejection; bronchitis; asthma; allergy; autoimmunity; sarcoidosis; bone marrow depression; bone marrow stimulation; sepsis; myasthenia gravis (MG); Parkinson's disease; skin disorders and irritation; arthritis; multiple sclerosis; neurodegenerative disorders (amyotrophic lateral sclerosis, chorea, Alzheimer disease); atherosclerosis; fibrosis; pain; chronic or acute inflammation.

The protective effect of the polypeptides of the invention can be achieved by prophylactic treatment. The protective effect can also be achieved by post-exposure treatment with the polypeptide. Similarly, the protective effect of the polypeptides is achieved against inflammatory processes as exemplified herein below.

The term "protecting" relate to reduction of degree of lesion or biological damage as measured by gross pathology or histopathological evaluation, subjective burning sensation or other accepted parameters for tissue damage, lesion, discomfort and pain.

The pharmaceutical compositions of the invention can be used for accelerated healing of or prevention of development of wounds including decubitus, ulcers (also induced by drugs), internal and external wounds, abscesses and various bleedings.

The pharmaceutical compositions of the invention are useful for treatment or protection against tissue damage including, but not limited to, neuronal, neurological, skin, hepatic, nephrologic, urologic, cardiac, pulmonary, gastrointestinal, lower and upper airways, visual, audiologic, spleen, bone, and muscle damage. Treatment or protection against tissue damage can be accomplished in the fetus, newborn, child, adolescent as well as in adults and old persons, whether the condition or disorder to be treated is spontaneous, of traumatic etiology or as a congenital defect.

It will be understood that the pharmaceutical compositions of the present invention can comprise the polypeptides of the current invention, or a derivative, analog or fragment thereof, or all possible combinations of two or more of these polypeptide derivatives, analogs, or fragments or other sources of the polypeptide of the current invention. Thus, the pharmaceutical compositions can comprise one or more isolated polynucleotides, one or more expression vectors, or one or more host cells or any combination thereof, according to the principles of the present invention.

Determination of a therapeutically effective amount of a polypeptide is well within the capability of those skilled in the art, especially in light of the detailed disclosure provided herein.

Toxicity and therapeutic efficacy of the polypeptides described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, for example, Fingl et al., 1975, in The Pharmacological Basis of Therapeutics, Ch. 1 p. 1, the contents of which are hereby incorporated by reference in their entirety).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, depend on the subject being treated, the severity of the affliction, the manner of administration, the judgment of the prescribing physician, and all other relevant factors. Determination of the exact dose to be administered is conducted by methods known to a person of skill in the art.

It is further understood that the polypeptides of the invention can be formulated or administered together with additional active ingredients as required to treat the condition of the patient.

It should be understood that in addition to the ingredients particularly mentioned above the formulations of this invention may include other agents or excipients conventional in the art having regard to the type of formulation in question, for example those suitable for oral administration may include flavoring agents.

It will be apparent to those skilled in the art that various modifications and variations can be made in the compositions, use and preparations of the present invention without departing from the spirit or scope of the invention.

For administration to mammals, and particularly humans, it is expected that in the case of medications, the physician or other qualified healthcare provider may determine the actual dosage and duration of treatment, which will be most suitable for an individual and can vary with the age, weight and response of the particular individual. It will be appreciated that in the case of non-prescription (e.g. "over-the-counter") medications, foods, food products, food supplements, cosmetic and personal care compositions, the amount may be determined at the discretion of the user, optionally with guidance from the labeling or from an appropriate health care provider or other advisor.

It is to be understood that repeated use of reference characters in the present specification and drawings is intended to represent the same or analogous features of the invention.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In the claims articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise.

Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein.

Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format Although described with specific examples, the present invention provides for some embodiments comprising variations of the components described above.

Accordingly, variations, omissions, substitutions, and changes may be made by those skilled in the art without departing from the spirit of the present invention.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLE 1

Effect of UBE on Carrageenan-Induced Hind Paw Swelling

Male CD1 mice were intravenously (i.v.) injected with the indicated doses of the UBE polypeptide having the sequence SMPPIVRFDHPFLFIIFEEHTQSPLFVGKVVDPTHK (SEQ ID NO:2). Thirty minutes thereafter, each animal was injected with carrageenan (50 µl of 3 mg/ml into each hindpaw). The animals were evaluated for the difference between the degree of swelling (mm) after 3 hours and prior to carrageenan injection.

FIG. 1 shows a significant reduction in carrageenan-induced inflammation following i.p. administration of UBE.

EXAMPLE 2

Effect of UBE on Experimental Autoimmune Encephalitis (EAE)

Female C57BL/6 mice were injected subcutaneously into 4 sites on the back, adjacent to each of the forelimbs and hindlimbs (total amount 200 µl) with a myelin oligodendritic glycoprotein (MOG) 35-55 fragment emulsified with complete Freund's adjuvant. Thereafter, each animal was i.p. injected with pertusis toxin (PTX; 200 ng/mouse) in PBS and an additional PTX injection was repeated 2 days later, which is a standard protocol for initiating experimental autoimmune encephalomyelitis (EAE) in mice. UBE polypeptide (SEQ ID NO:2) was intraperitoneally (i.p.) injected (0.3 µg/kg, thrice a week) five days after MOG immunization (day of onset of symptoms). The animals were evaluated for neurological score from 0 (no effect) to 6 (severe neurological symptoms including paralysis). Results are the mean±SE of neurological score (sum of all scores divided by the number of animals in each experimental group) at each of the indicated time intervals after MOG injection.

Figure 2:
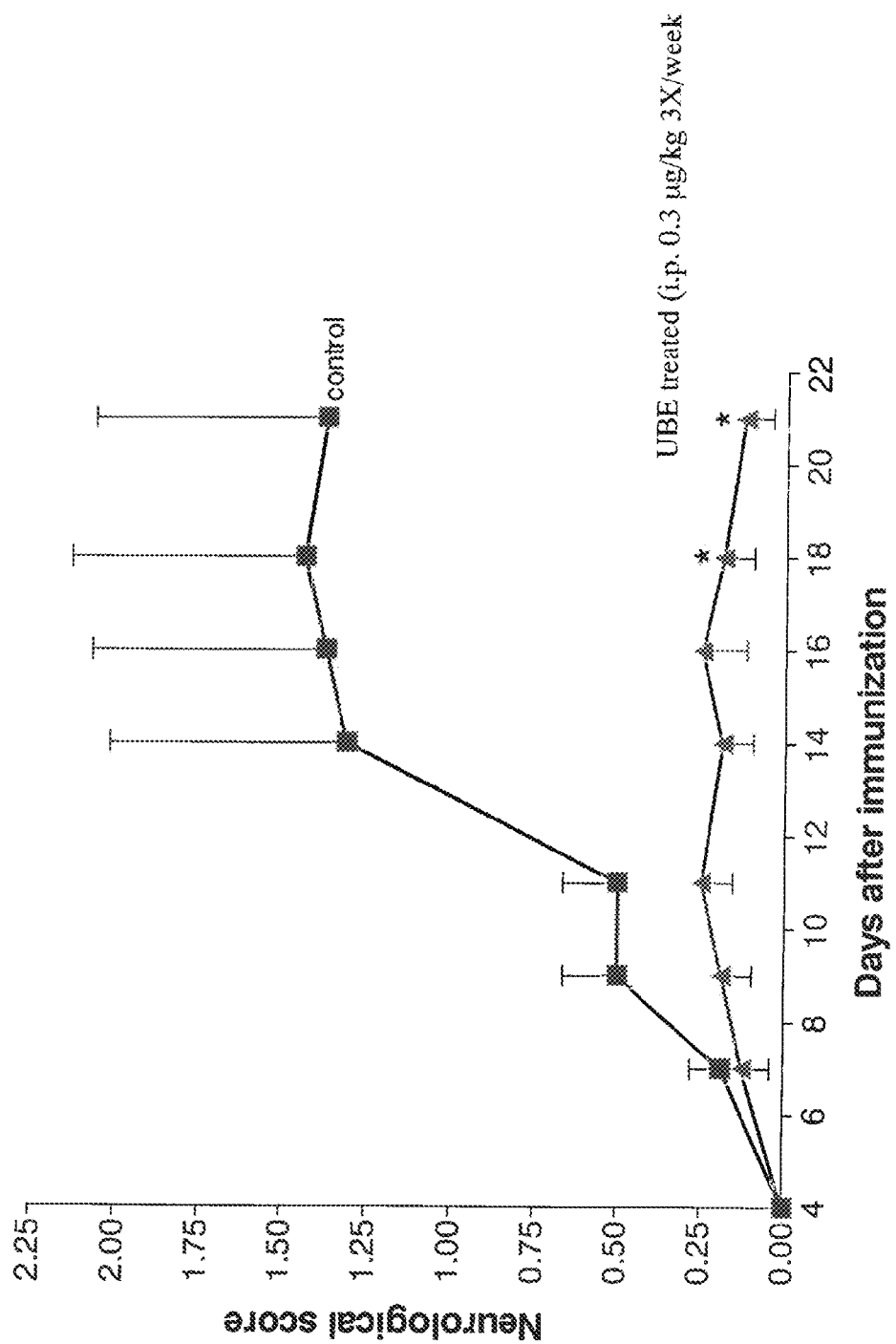
FIG. 2 shows the effect of UBE on the neurological score of mice having experimental autoimmune encephalitis (EAE).

FIG. 2 shows that UBE when i.p. administered to EAE mice reduced the neurological symptoms associated with the disease.

EXAMPLE 3

Effect of UBE Derivatives on Experimental Autoimmune Encephalitis

Female C57BL/6 mice were injected subcutaneously into 4 sites on the back, adjacent to each of the forelimbs and hindlimbs (total amount 200 µl) with a myelin oligodendritic glycoprotein (MOG) 35-55 fragment emulsified with complete Freund's adjuvant. Thereafter, each animal was i.p. injected with pertusis toxin (PTX; 200 ng/mouse) in PBS and an additional PTX injection was repeated 2 days later. Four days after MOG immunization, each mouse received i.p. injections (1 µg/kg, thrice a week) of each of the following polypeptides:

```
(SEQ ID NO: 2; designated UBE)
SMPPIVRFDHPFLFIIFEEHTQSPLFVGKVVDPTHK;

(SEQ ID NO: 1; designated UBE1)
YSMPPIVRFDHPFLFIIFEEHTQSPLFVGKVVDPTHK;

(SEQ IS NO: 3; designated UBE-N)
MPPIVRFDHPFLFIIFEEHTQSPLFVGKVVDPTHK;
and (SEQ ID NO: 4; designated UBE-C)
SMPPIVRFDHPFLFIIFEEHTQSPLFVGKVVDPTH.
```

The animals were evaluated for neurological score from 0 (no effect) to 6 (severe neurological symptoms including paralysis). Results are the mean±SE of neurological score (sum of all scores divided by the number of animals in each experimental group) at each of the indicated time intervals after immunization.

Figure 3:
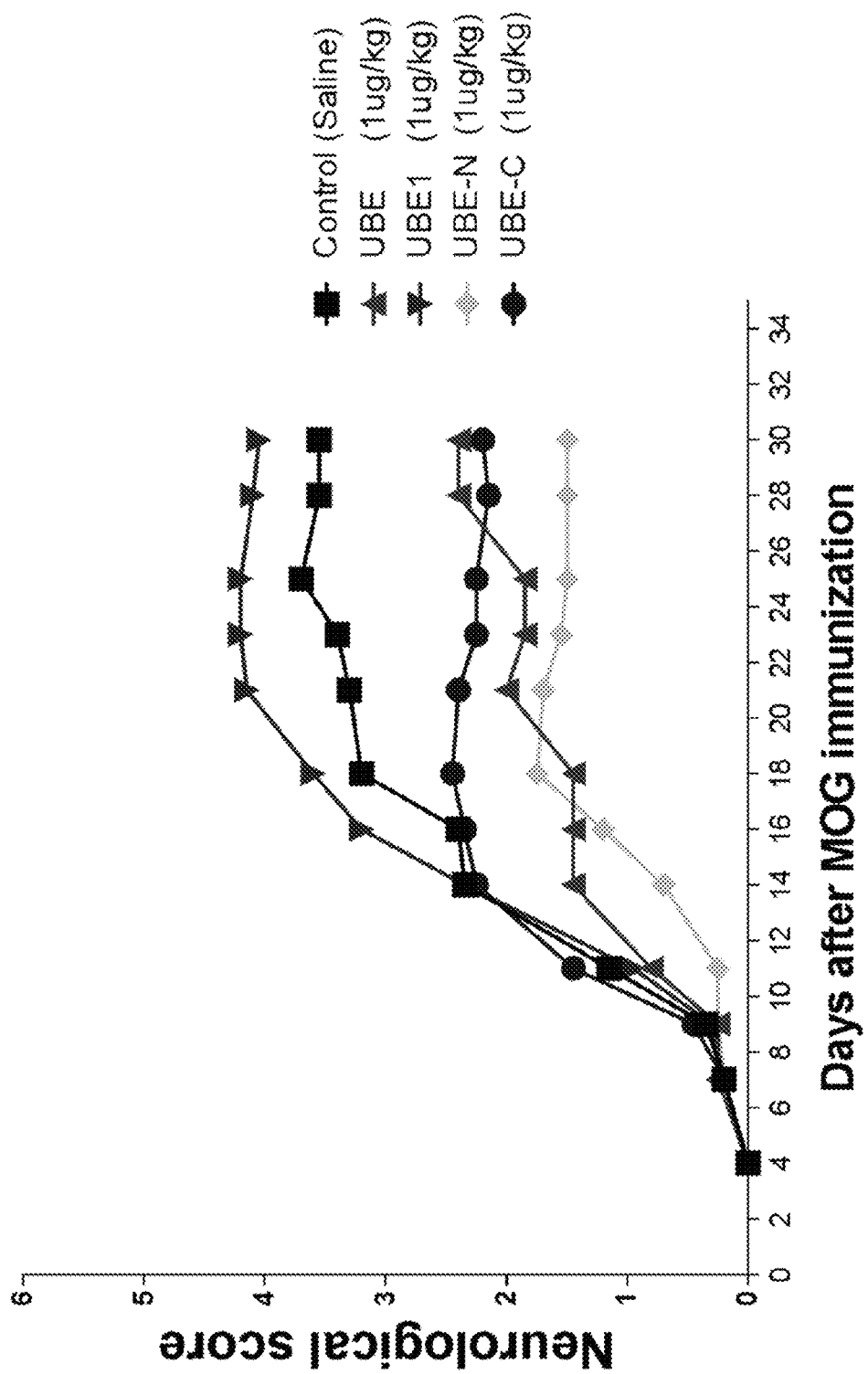
FIG. 3 shows the effect of UBE derivatives on the neurological score of mice having experimental autoimmune encephalitis.

FIG. 3 shows that UBE, UBE-N, or UBE-C when i.p. administered to EAE mice reduced the neurological symptoms associated with the disease.

EXAMPLE 4

Effect of UBE on Systemic Lupus Erythematosus

An animal model for Systemic Lupus Erythematosus was used to determine the effect of UBE on the manifestations of this disease.

MRL/lpr mice develop a lupus-like syndrome spontaneously. UBE (SEQ ID NO:2) (1 µg/kg) was administered to female MRL/lpr mice thrice a week, starting at age of 12 weeks. Urine was obtained by spontaneous urination and the levels of protein (mg/dl) and erythrocytes (cells/dl) in the urine were evaluated throughout the treatment period (4 weeks) using commercial sticks.

Figure 4:
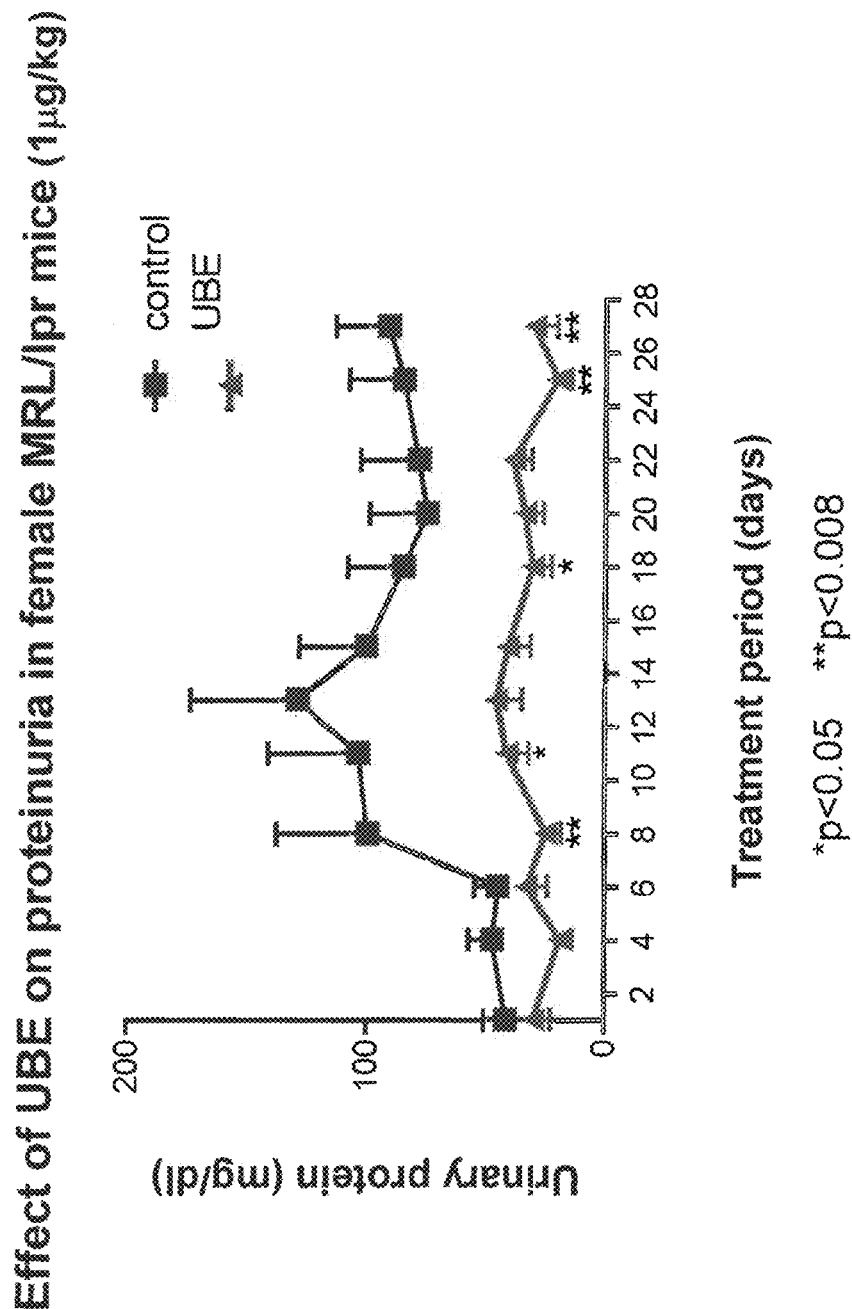
FIG. 4 shows the effect of UBE on proteinuria in MRL/lpr mice having spontaneous lupus-like syndrome.

FIG. 4 shows a significant reduction in proteinuria following UBE administration to MRL/lpr mice.

Figure 5:
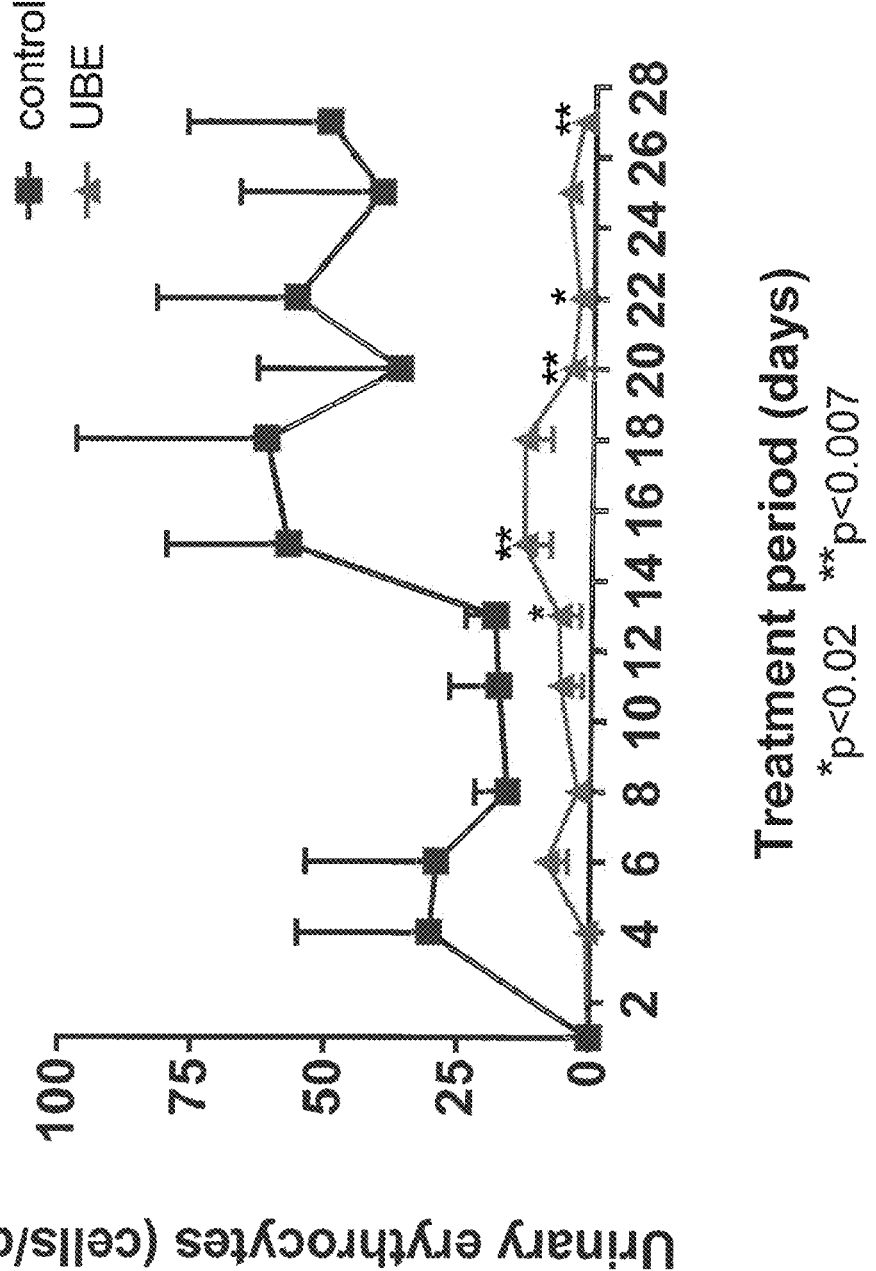
FIG. 5 shows the effect of UBE on microhematuria in MRL/lpr mice having spontaneous lupus-like syndrome.

FIG. 5 shows a significant reduction in urinary microhematuria following UBE administration to MRL/lpr mice.

In order to determine the levels of anti-dsDNA antibodies, blood was obtained by cardiac puncture of the MRL/lpr mice after 4 weeks of UBE treatment, and the serum levels of anti-dsDNA antibodies were evaluated using a commercial ELISA kit.

FIG. 6 shows a significant reduction in anti-dsDNA antibodies in the blood levels of MRL/lpr mice after UBE administration. FIG. 6A shows the cumulative antibody response, while FIGS. 6B, 6C, 6D and 6E show specific IgM, IgG1, IgG2a and IgG2b responses, respectively. Serum levels of anti-dsDNA antibodies were determined by ELISA with the aid of a commercial kit (Euroimmun, Lubeck, Germany) following the manufacturer's instructions and detection antibodies were purchased for use with same (Bethyl Laboratories, Montgomery, Tex., USA).

Figure 7B:
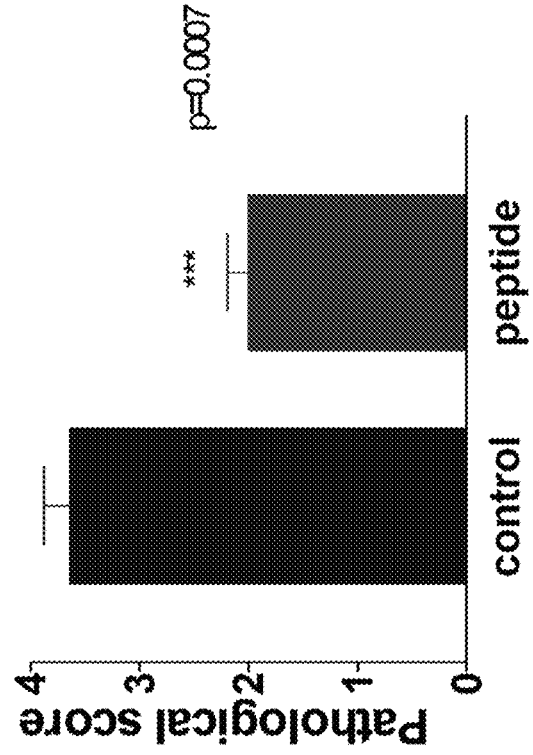
FIG. 7A and FIG. 7B, respectively show the quantitative histopathology analysis of the kidneys in control and UBE treated mice. Representative histopathologies of the tubular and interstitial areas in control versus UBE treated mice is shown FIG. 7C and FIG. 7D, versus FIG. 7E and FIG. 7F, respectively.
Figure 7A:
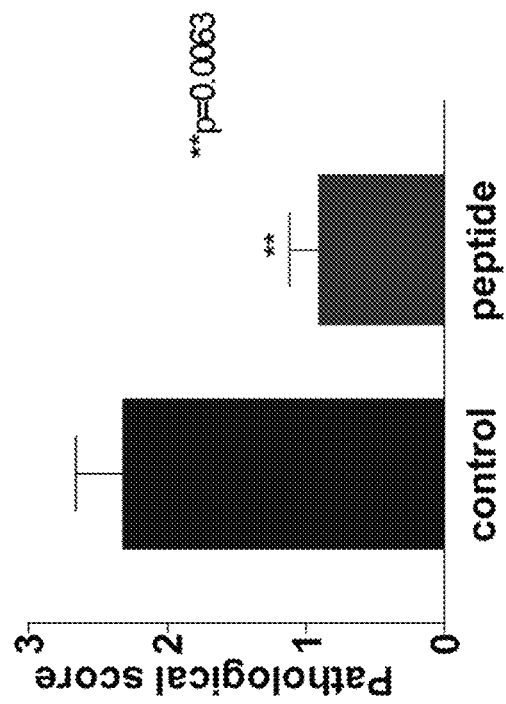
Figure 7D:
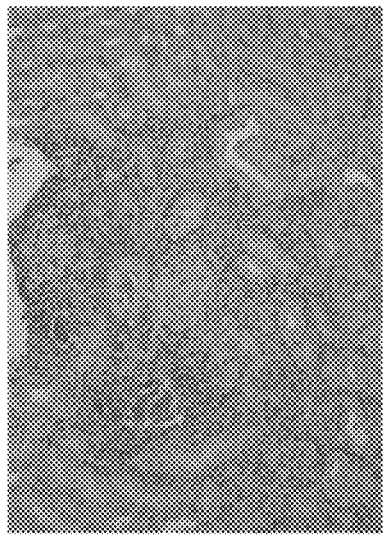
Figure 7F:
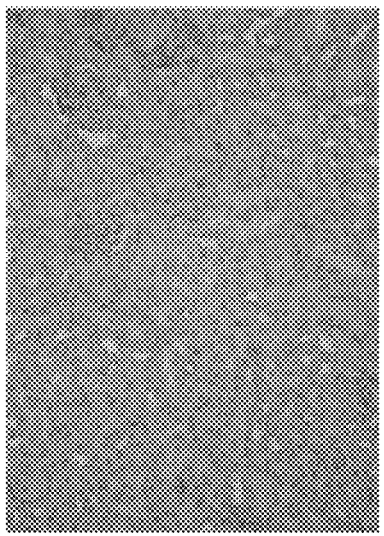
Figure 7C:
Figure 7E:
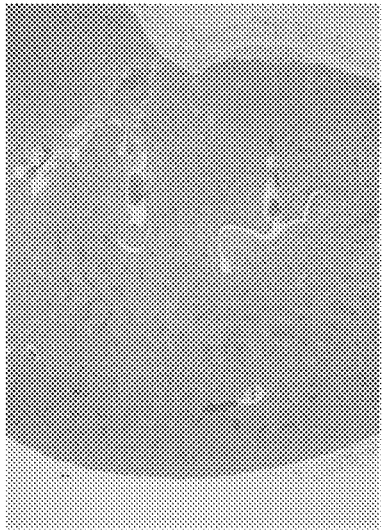

Quantitative histopathology analysis of the kidneys was also performed. The kidneys of the mice after 4 weeks of UBE treatment were removed, fixed in formalin, sliced, and stained by H&E and by periodic acid shift stain. Representative histophathologies of the glomeruli and tubulointerstitial areas in control versus UBE treated mice is shown FIGS. 7C and 7D, versus 7E and 7F at 2× and 20×, respectively. The quantitative histopathology analysis is presented in FIG. 7A and FIG. 7B, respectively. A significant reduction in the pathological score of both the glomeruli and tubulointerstitial areas following UBE administration to MRL/lpr mice was shown.

To evaluate the effect of UBE on lymphocyte function in MRL/lpr mice, peripheral lymph nodes and spleen cells were isolated from the control and UBE-treated mice and subjected to FACS analysis probing for CD4, CD8 and B220 marker expression (FIG. 8). Peripheral lymph node cells were positively selected for CD3 expression and the percent of CD3+ cells, which were negative for CD4− and CD8− expression were evaluated. Representative results from control and UBE treated animals are shown in FIGS. 8A and 8B, respectively. Quantitative results are graphically depicted in FIG. 8E, where it was found that UBE treatment dramatically reduced the double negative CD4−CD8− cells (expressed as percent CD3+) in peripheral lymph nodes. Spleen cells were similarly evaluated and representative results from control and UBE treated animals are shown in FIGS. 8C and 8D, respectively. Quantitative results are graphically depicted in FIG. 8F, where it was found that UBE treatment dramatically reduced the double negative CD4−CD8− cells.

In parallel, peripheral lymph node cells were positively selected for B220+ expression. Representative results from control and UBE treated animals are shown in FIGS. 8G and 8H, respectively. Quantitative results are graphically depicted in FIG. 8I, where it was found that UBE treatment dramatically reduced the percent of B220+ in peripheral lymph nodes. Spleen cells were similarly evaluated and representative results from control and UBE treated animals are shown in FIGS. 8I and 8J, respectively. Quantitative results are graphically depicted in FIG. 8J, where it was found that UBE treatment dramatically reduced the percent of B220+ cells, as well.

Figure 9A:
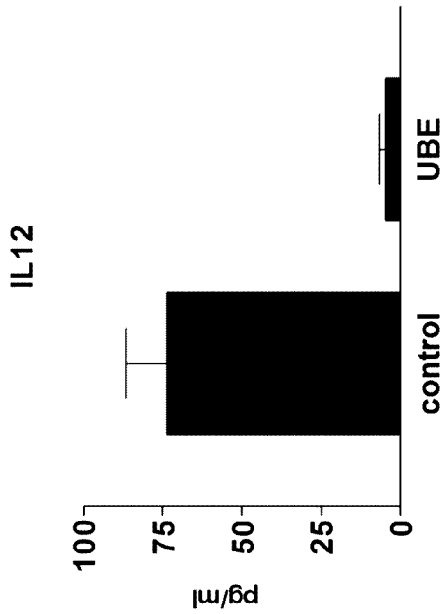
FIG. 9A and FIG. 9B show serum cytokine levels in UBE-treated and control mice, with specific levels of IL17 (FIG. 9A) and IL12 (FIG. 9B) shown as the mean±sem (n=11).
Figure 9B:
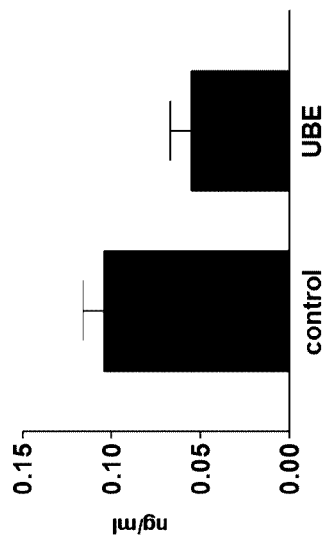
Figure 9C:
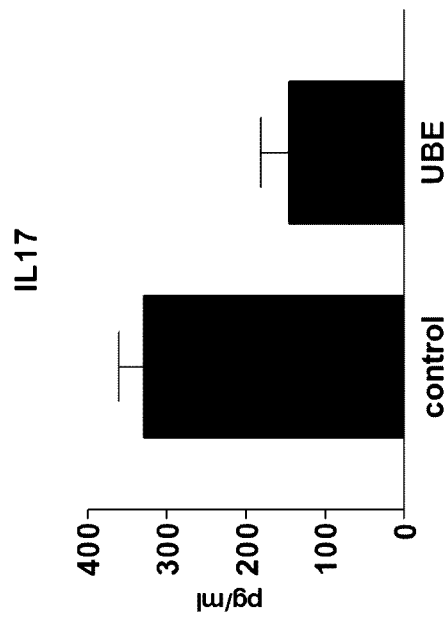
FIG. 9C and FIG. 9D plot the cytokine levels from CD4 cells isolated from naive mice and activated with anti CD3 anti CD28 antibodies with and without UBE (ing/nil) treatment, with specific levels of IL-17 (FIG. 9C) and IL-12 (FIG. 9D) shown.
Figure 9D:
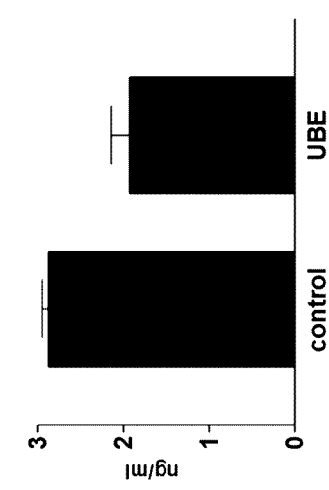

To assess the effect of UBE on cytokine production in control versus UBE treated mice, serum samples were collected at the endpoint of the experiment and specific cytokine levels were assessed by ELISA. Specific levels of IL17 (FIG. 9A) and IL12 (FIG. 9B) in serum was determined by using commercial kits, following the manufacturer's instructions. Results were represented as the mean±sem (n=11). In addition, isolated CD4 cells from naive mice were activated with anti CD3 anti CD28 antibodies for 72h in the presence of UBE (1 ng/ml) and supernatants were collected and similarly assessed for IL-17 (FIG. 9C) and IL-12 (FIG. 9D) levels. Results are represented as the mean±sem (n=6). P=0.0022, <0.0001, 0.0015 and 0.012 for A, B, C and D, respectively.

EXAMPLE 5

Effect of UBE at Advanced Stage of Systemic Lupus Erythematosus

UBE (SEQ ID NO: 2; 1 μg/kg) was administered to male MRL/lpr mice thrice a week, starting at age of 22 weeks. At this age the mice are acutely affected and show a high level of proteinuria. Urine was obtained by spontaneous urination and the animals' urinary protein levels (mg/dl) were evaluated throughout the treatment period (22 days) using a commercial stick.

FIG. 10 shows a significant reduction in proteinuria following UBE administration to MRL/lpr mice.

EXAMPLE 6

Effect of UBE on Systemic Lupus Erythematosus as Determined by a Second Model

Another animal model routinely used in evaluating milder Systemic Lupus Erythematosus pathogenesis was similarly evaluated to determine the effect of UBE on the manifestations of this disease in this model.

Figures 11A, 11B:
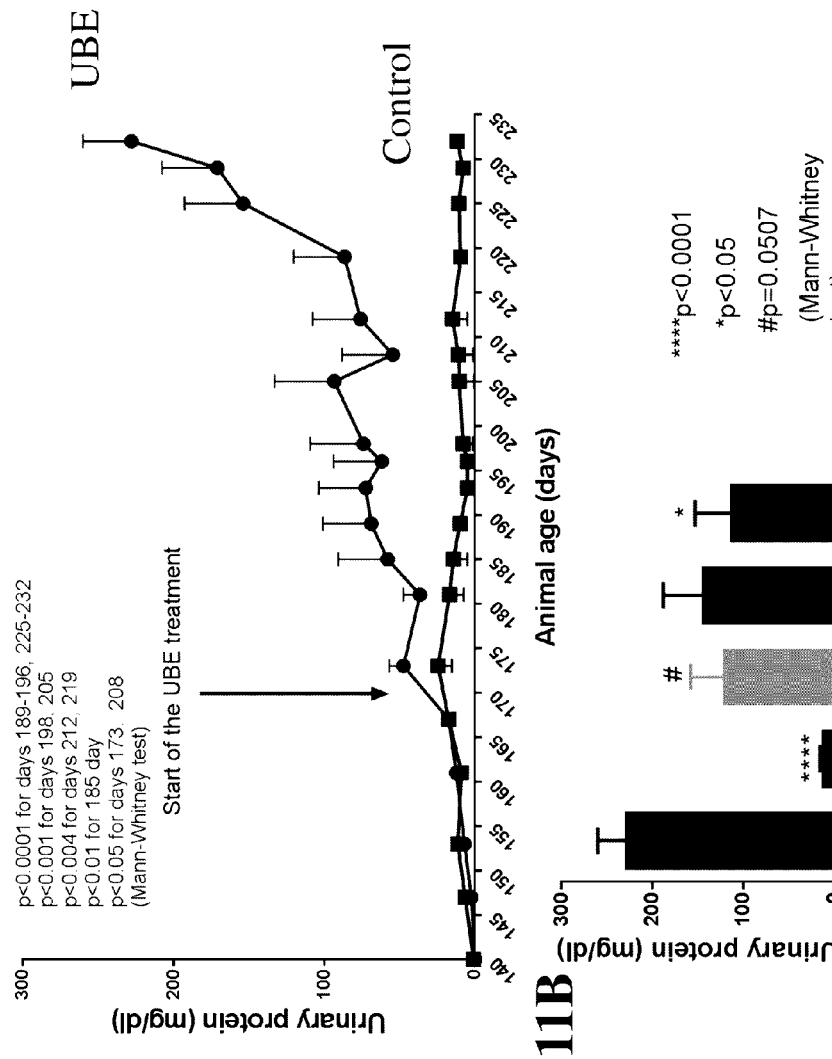
FIG. 11A plots proteinuria in NZBW/F1 mice, a second model having spontaneous lupus-like syndrome in UBE treated (0.3 µg/kg daily) and control mice.
FIG. 11B further extends the results in FIG. 11A, comparing UBE treated mice given higher dosages of the UBE peptide (1 µg/kg and 3 µg/kg) also in comparison to dexamethasone treatment.

Female NZBW/F1 mice develop a lupus-like syndrome spontaneously. UBE (SEQ ID NO:2) (0.3 μg/kg) was administered to female NZBW/F1 mice daily (except for Saturday and Holidays), starting at the indicated time point (170 days) (n=10). Urine was obtained by spontaneous urination and the levels of protein (mg/dl) in the urine were evaluated throughout the treatment period using commercial sticks. FIG. 11A shows control mice versus those receiving UBE treatment, where the rise in urinary protein levels seen in controls is abrogated in UBE treated animals, even at the low dosage provided. This result was further extended by also comparing UBE treated mice given higher dosages of the UBE peptide (1 μg/kg and 3 μg/kg) and compared to dexamethasone treatment, as well. Each treatment reduced proteinuria in a significant manner, but surprisingly, very low concentration UBE treatment provided the most ideal results in this model.

Quantitative histopathology analysis of the kidneys and lungs were also performed for this model (FIG. 12A-D). Kidneys were removed from control and UBE treated mice (0.3 lug/kg) then fixed in formalin, sliced, and stained by H&E. Representative histopathologies of the control versus UBE treated mice is shown FIGS. 12A versus 12B at 10× magnification, respectively. Note glomerular sclerosis (GS), thickening glomerular mesangium (G), protein accumulation in tubular lumen (PC), interstitial fibrosis (I) and perivascular lymphoid infiltration (lymphoid) in the control (12A) while normal appearance of kidney in the UBE-treated group (12B). The quantitative histopathology analysis with regard to tubular and interstitial damage is presented in FIG. 12C and FIG. 12D, respectively. A significant reduction in the pathological score of both the tubular and interstitial areas following UBE administration to NZBW/F1 mice was shown.

Figure 12B:
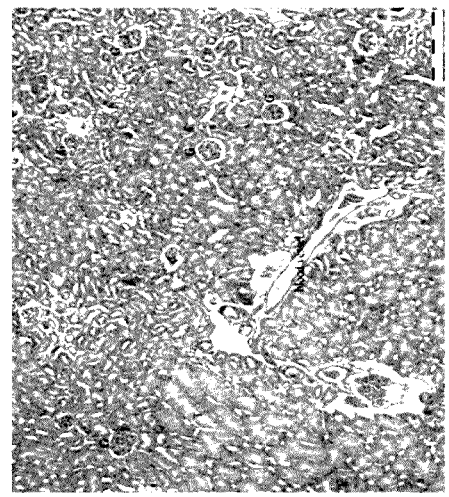
FIG. 12A, FIG. 12B, FIG. 12C and FIG. 12D show the quantitative histopathology analysis of kidneys and lungs in UBE-treated and control NZBW/F1 mice. Representative histopatologies are presented in FIG. 12A and FIG. 12B, respectively for UBE-treated and control mice and quantitative results are plotted in FIG. 12C and FIG. 12D in terms of the tubular versus interstitial damage, respectively.
Figure 12A:
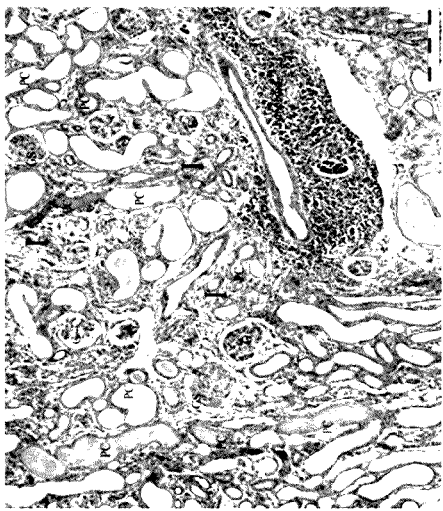
Figure 12D:
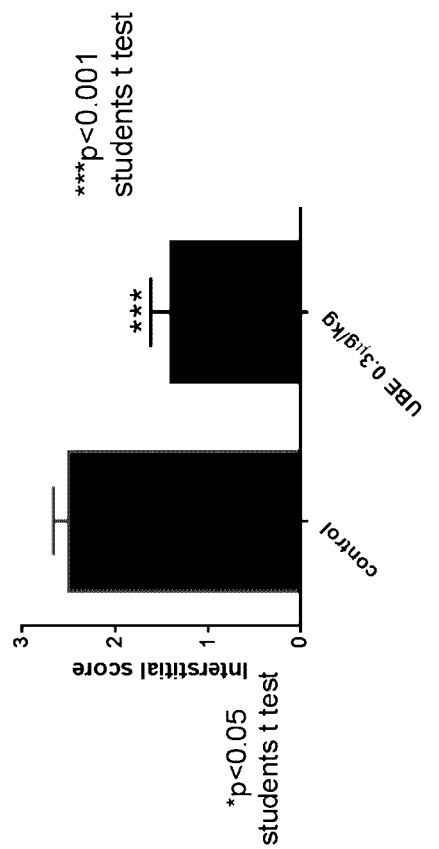
Figure 12C:
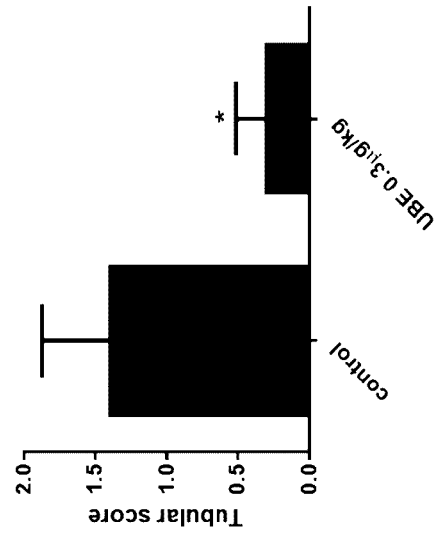
Figure 12E:
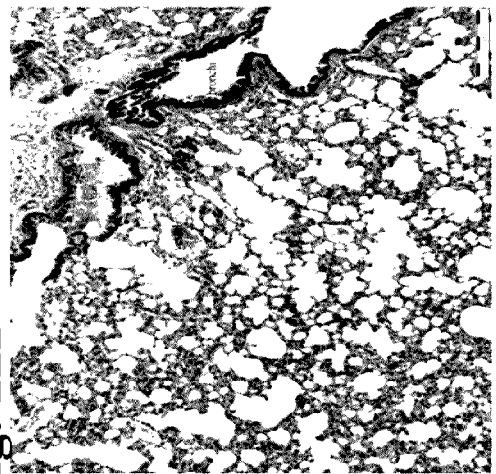
FIG. 12E and FIG. 12F, respectively show representative lung histopathologies in control versus UBE-treated NZBW/F1 mice and results are quantitatively plotted in FIG. 12G.
Figure 12F:
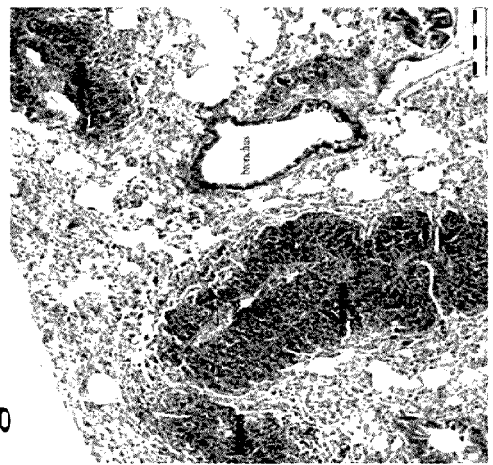
Figure 12G:
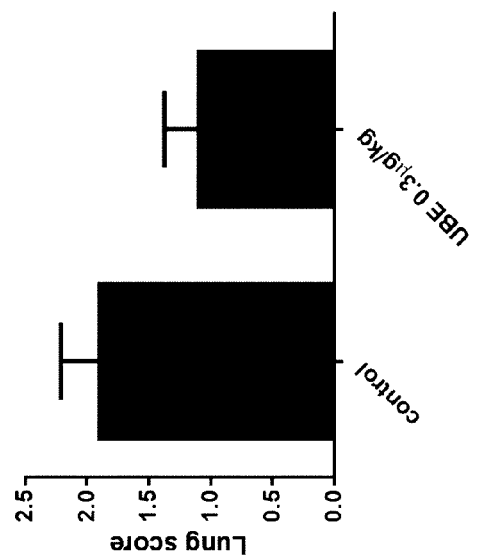

Quantitative histopathology analysis of the lungs was also performed for this model (FIG. 12E-G). Representative histopathologies of control versus UBE treated mice (0.3 μg/kg) is shown FIGS. 12E versus 12F at 10× magnification, respectively. Note heavy perivascular lymphoid infiltration (lymphoid) in the control samples (FIG. 12E) while normal appearance in the UBE-treated group (FIG. 12F). The quantitative histopathology analysis with regard to lung parenchymal damage is presented in FIG. 12G. A significant reduction in the pathological score following UBE administration to NZBW/F1 mice was shown.

In order to determine the levels of anti-dsDNA antibodies, blood was obtained by cardiac puncture of the NZBW/F1 mice at the indicated endpoint in UBE treatment, and the serum levels of anti-dsDNA antibodies and BLys (B lymphocyte stimulator) levels were determined by ELISA using a commercial kit (R&D Systems, Minneapolis, Minn., USA).

Figure 13A:
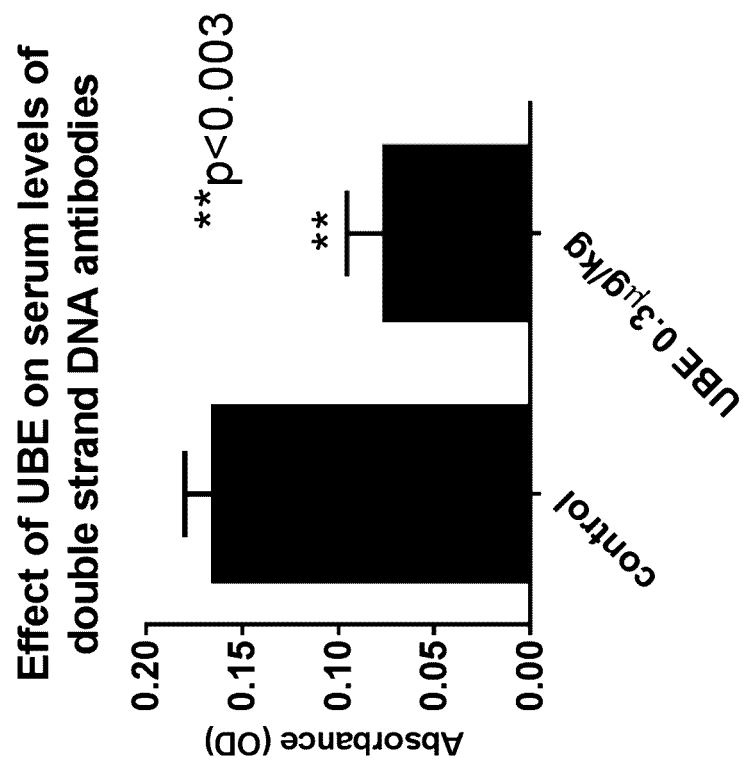
FIG. 13A and FIG. 13B show significant reduction in serum BLys and anti-dsDNA antibodies levels of NZBW/F1 mice, respectively, after UBE administration (0.3 µg/kg).
Figure 13B:
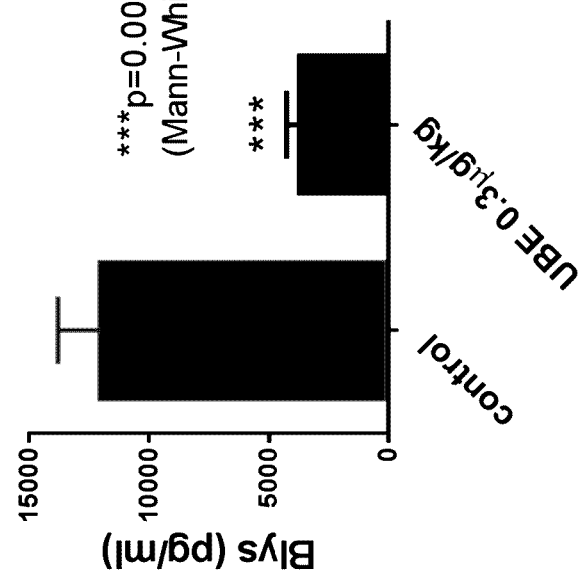

FIG. 13A and FIG. 13B show a significant reduction in serum BLys and anti-dsDNA antibody levels of NZBW/F1 mice, respectively, after UBE administration (0.3 μg/kg).

To evaluate the effect of UBE on lymphocyte function in NZBW/F1 mice, spleen cells and blood samples were isolated from control and UBE-treated (0.3 microgram per kilogram) mice and subjected to FACS analysis of double negative CD4−CD8− (expressed as percent CD3+) (FIG. 14). A significant reduction of double negative CD4−CD8− was observed in the spleens of UBE treated animals (FIG. 14B) as compared to controls (FIG. 14A), respectively. Quantitative results are graphically depicted in FIG. 14C, where it was found that UBE treatment (0.3 µg/kg) dramatically reduced the double negative CD4−CD8− cells in the spleen.

Blood cells were similarly evaluated and representative results from control and UBE treated animals (0.3 µg/kg) are shown in FIGS. 14D and 14E, respectively. Quantitative results are graphically depicted in FIG. 14F, where it was found that UBE treatment dramatically reduced the double negative CD4−CD8− cells in the blood.

Figures 15A, 15B, 15C:
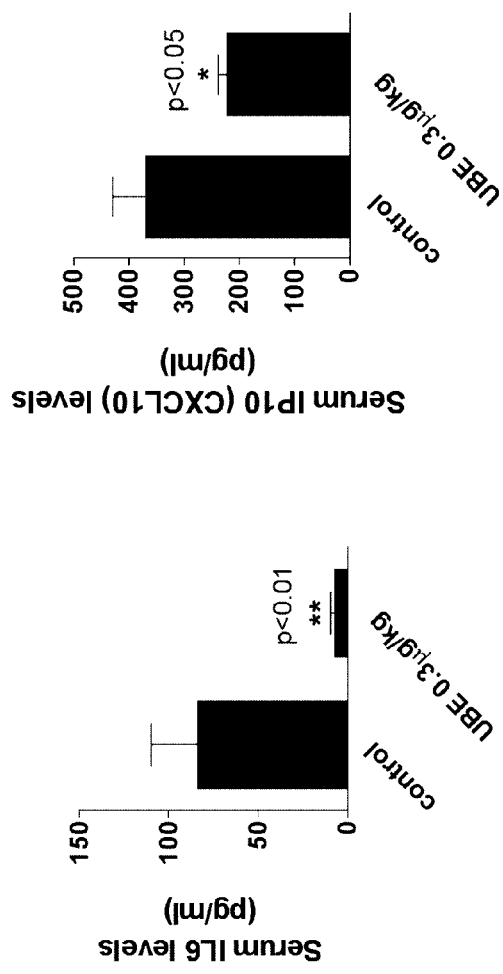
FIG. 15A, FIG. 15B and FIG. 15C plot the effect of UBE on serum cytokine levels in control versus UBE treated mice (0.3 µg/kg), for IL6 (FIG. 15A) IP10 (FIG. 15B) and MCP1 (FIG. 15C).

To assess the effect of UBE on cytokine production in control versus UBE treated mice (0.3 µg/kg), serum samples were collected at the endpoint of the experiment and specific cytokine levels were assessed by ELISA. Specific levels of IL6 (FIG. 15A) IP10 (FIG. 15B) and MCP1 (FIG. 15C) in serum was determined by using commercial kits.

EXAMPLE 7

Effect of Administration of UBE or UBE1 on Arthritic Mice

Chick collagen type II (2.0 mg) was incubated overnight in 0.01 M acetic acid (0.9 ml) at 4° C. The resulting solution was emulsified with equal volume (1.0 ml) of incomplete Freund's Adjuvant containing 5.0 mg heat-killed *Mycobacterium tuberculosis*. Thereafter, the animal was injected intradermally in the tail base with 100 µl of the emulsion and an additional immunization was repeated 21 days later. Five days later, UBE or UBE1 polypeptide were administered (1 µg/kg thrice a week). The animals were evaluated for the difference in joint thickness (mm) between the indicated time intervals and prior to immunization.

FIG. 16 shows a reduction in joint swelling in both UBE- and UBE1-treated mice.

EXAMPLE 8

Effect of UBE on Lymphocyte Proliferation In Vitro

T-lymphocytes were harvested from lymph nodes of female C57B1/6 mice by standard methodology and seeded (1.3×10$^6$ cells/ml) in 96 well plate (1000). Thereafter, UBE was added to the culture at the indicated concentrations and incubated for 96 hours (6% $CO_2$, 37° C.). The medium containing the polypeptide was replaced after 48 hours of incubation. Viable cells (trypan blue staining) were counted a light microscope.

Figure 17:
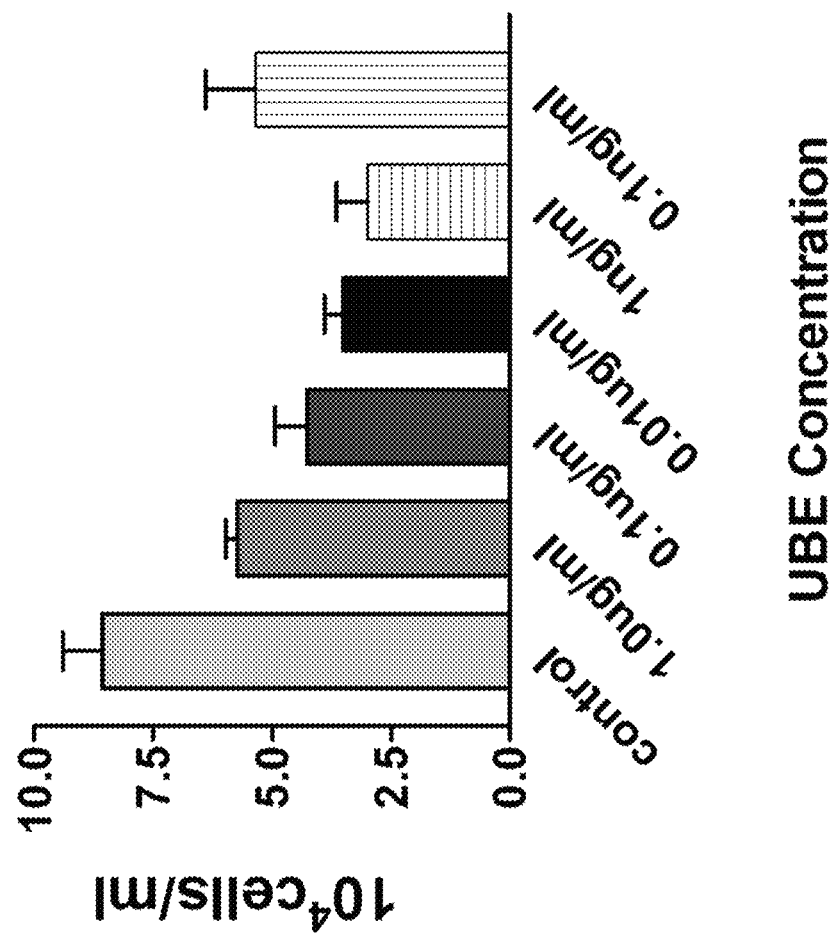
FIG. 17 shows the effect of UBE on lymphocyte proliferation in culture.

FIG. 17 shows a maximal effect of UBE on T cell proliferation at a concentration of 1 ng/ml.

EXAMPLE 9

Effect of UBE on HaCaT Keratinocyte Proliferation

Cells (1.6×10$^4$/ml) were seeded (100 µl) in culture medium in 96 well plate. Twenty four hours later UBE was added at the indicated concentrations. Cell viability was determined by the MTT assay.

Figure 18:
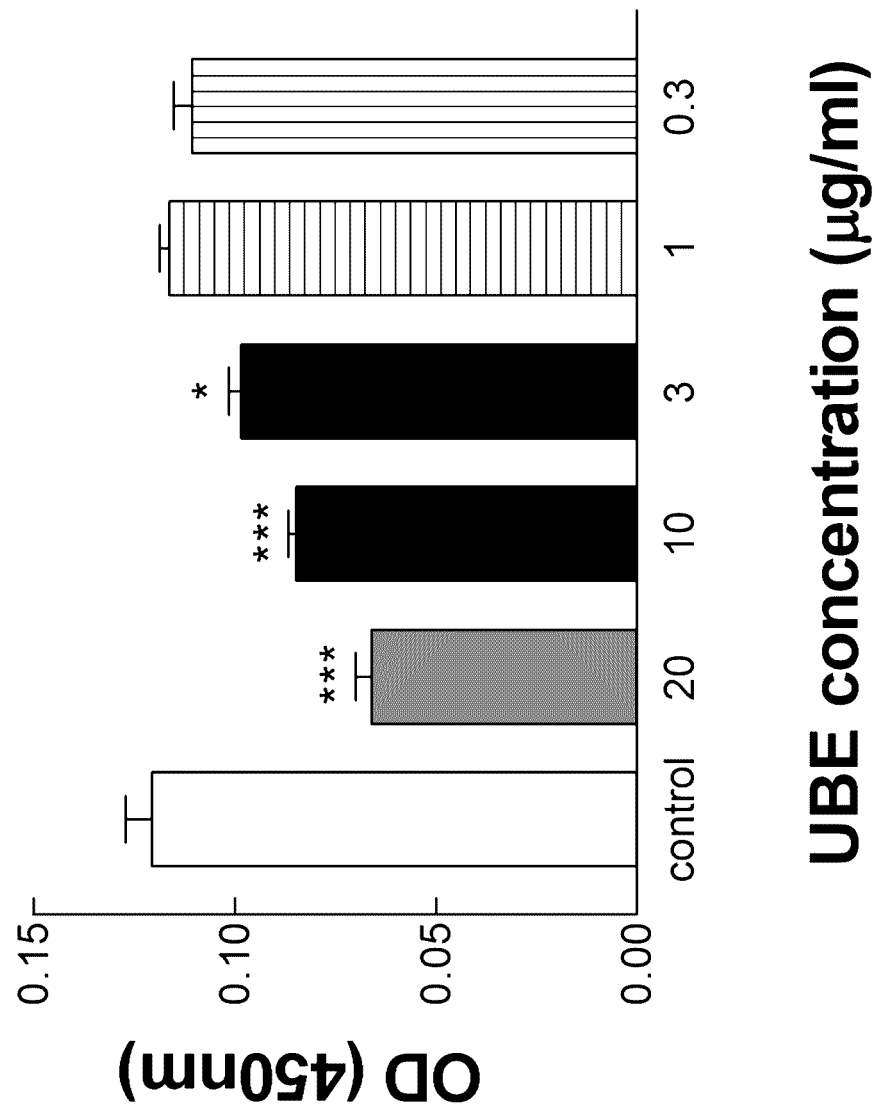
FIG. 18 shows the effect of UBE on HaCaT keratinocyte proliferation.

FIG. 18 demonstrates the anti-proliferative effect of UBE on cultured keratinocytes.

EXAMPLE 10

Effect of UBE on Oxidative Burst of Peritoneal Macrophages

Macrophages were harvested by peritoneal lavage of female C57BL/6 mice i.p. injected with thioglycolate. 0.2 ml cells (3×10$^5$/ml), luminol (200 µM), horseradish peroxidase (1.0 unit/ml) and UBE were suspended in Hank's balanced salt solution (HBSS) (final concentrations of the peptide in the reaction mixture are indicated in the figure). The reaction started by the addition of 1 µM phorbol myristate acetate. The reaction was performed in a 96-well plate. Luminescence was measured by Tecan spectrofluoro Plus.

Figure 19:
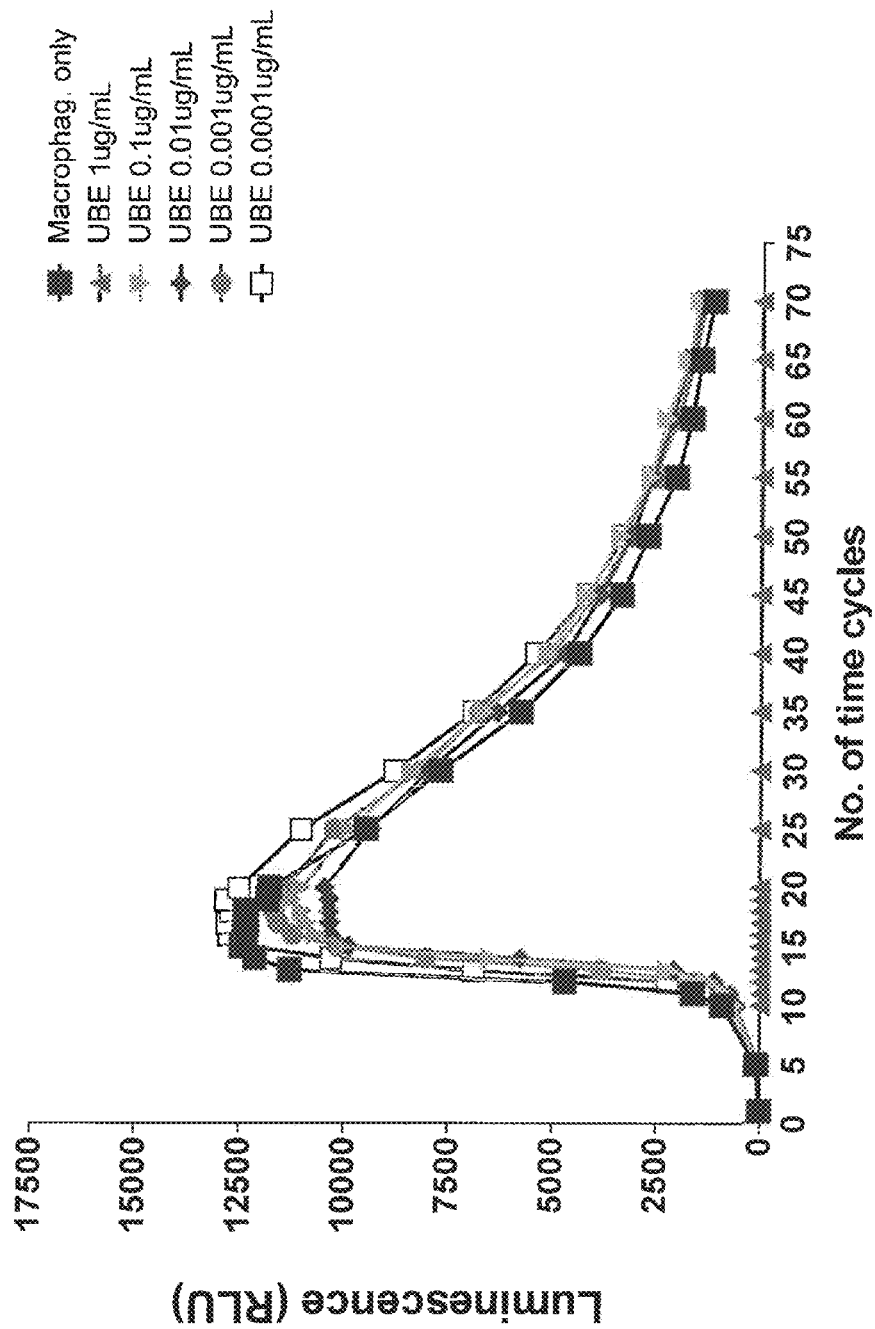
FIG. 19 shows the effect of UBE on oxidative burst of peritoneal macrophages.

FIG. 19 shows that 1 µg/ml UBE suppressed oxidative burst of peritoneal macrophages.

EXAMPLE 11

Effect of UBE on LPS Induced Sepsis in Mice

Female C57B1/6 mice 7-8 weeks of age were injected i.p with LPS 1.2 mg/mouse. Thereafter (within 1 hour) UBE peptide as depicted by SEQ ID NO: 2 was injected i.v. (100 µl) at different doses; control group received PBS. Survival of mice was monitored. n=10 for control group, n=9 for each UBE-treated group.

Figures 20A, 20B:
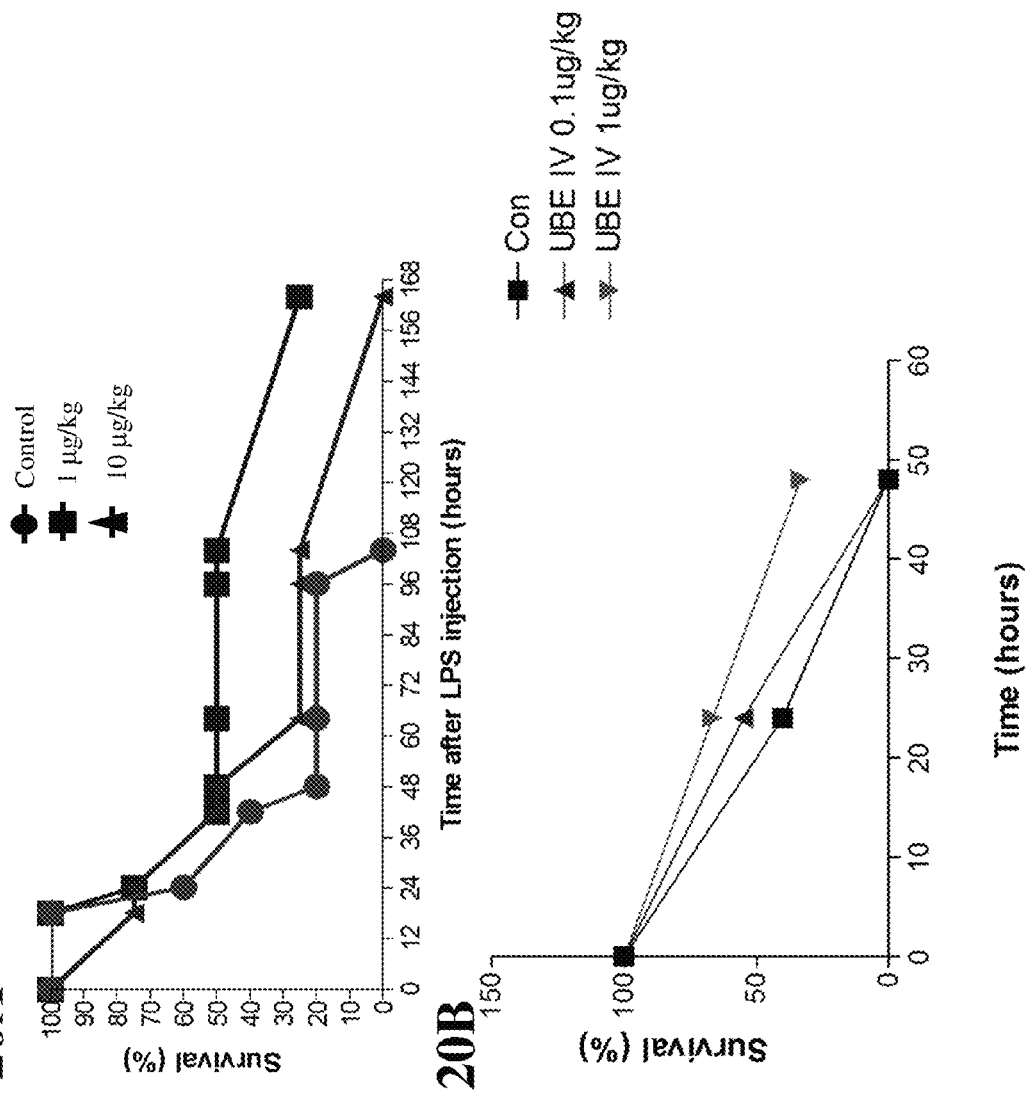
FIG. 20A and FIG. 20B shows the effects of UBE on LPS induced models of sepsis in mice.

The results are shown in FIG. 20B. Injection of UBE reduced by 33% the LPS-induced mortality as observed 48 hours after LPS stimulation.

In a second protocol, mice were injected i.p. with LPS (dissolved in saline solution) at a dose of 1.2 mg/mouse, followed by i.p. injection of UBE at a dose of 1.0 or 10.0 µg/kg after 30 minutes. UBE treatment was repeated after 24 hours (n=4 for UBE-treated groups and n=5 for controls).

FIG. 20A demonstrates that treatment with both 1.0 µg/kg and 10 µg/kg provided for survival of approximately 50% of the mice treated, whereas only 20% of controls survived to 50 hours post LPS injection. Both UBE dosages significantly prolonged survival in mice, as compared to controls.

EXAMPLE 12

Effect of UBE on Ovalbumin-Induced Asthma in Mice 20 ul of 5% Ovalbumin (OVA) was added to 8.75 ml of sterile saline, which was then added stepwise to a solution of 1.25 ml of 40 mg/ml ImjectAlum (Pierce), and subjected to rocking at room temperature for 30-60 minutes, to facilitate optimal alum absorption to the Ovalbumin (Alum/Ova). Female Balb/C mice were then injected with 200 ul of Alum/Ova i.p, according to the following protocol:

On Days 0 and 14, mice were injected i.p with OVA/Alum.

On day 24 mice were injected intranasally (i.n.) with. UBE/saline (50 ng/50 µl/mouse, 25 µl to each nostril) and then after one hour, mice were injected i.n with OVA (50 µg/50 µl/mouse, 25 µl to each nostril).

On Day 27, mice were injected i.n. UBE/saline (50 ng/50 µl/mouse, 25 µl to each nostril) and then 1 hour subsequently were again injected i.n. with OVA (50 µg/50 µl/mouse). Mice were then sacrificed on day 29, and bronchoalveolar fluid was obtained by lung lavage (1 ml of 10% FCS-heat inactivated in PBS), and the percent of eosinophils seen in lavage fluid versus white cell count was ascertained by microscopic evaluation of smears.

Figure 21:
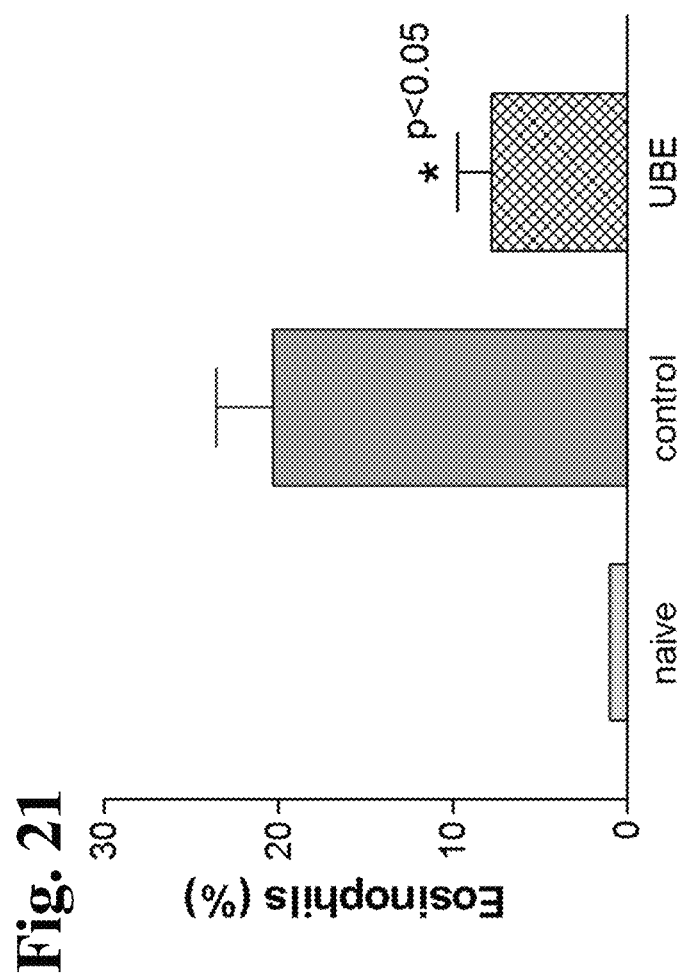
FIG. 21 shows the effects of UBE on an OVA-induced model of asthma in mice.

FIG. 21 demonstrates a dramatic reduction in eosinophil concentration in lavage fluid of mice treated with UBE as compared to controls, and the difference was statistically significant, as determined by the Student's t-test.

EXAMPLE 13

Effect of UBE on the Cytokine Profile in Human CD4+ Cells

Human CD4 cells were MACS separated from blood of healthy donors using the immunomagnetic separation system of Miltenyi, in accordance with manufacturer instructions. Cells were incubated (each well contained 0.5×10⁶/ 0.5 ml) with human IL2 (100 U/ml) and human anti CD3 antibodies (1 ug/ml) and human anti CD28 antibodies (1 ug/ml) with or without UBE (100 ng/ml) for 72 hours in a $CO_2$ (6%) incubator at 37° C. in multiwall plates. Thereafter plates were centrifuged and supernatants were collected and stored at −20° C. until cytokine analysis was conducted. Cytokines were determined by Multiplex system (BioRad).

*$p<0.02$, **$p<0.006$ using students t-test for comparison between UBE-treated and control cells.

Cytokines evaluated included IL6 (FIG. 22A), IL17A (FIG. 22B), IL21 (FIG. 22C), IL22 (FIG. 22D), IL23 (FIG. 22E), IL31 (FIG. 22F) and IFNγ (FIG. 22G). IL22, IL23 and IL31 were significantly reduced in UBE treated cells, as compared to controls and an overall trend in reduced inflammatory mediators was evident from these results, as well.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification. In addition, citation or identification of any reference in this application shall not be construed as an admission that such reference is available as prior art to the present invention.

The invention claimed is:

1. A method for treating inflammation in a subject in need thereof, said method comprising administering to a subject suffering from a disease selected from the group consisting of an autoimmune disease, a degenerative neurological disease, a degenerative muscle disease, graft rejection, graft versus host disease, allergy, a musculo-skeletal inflammation and sepsis a therapeutically effective amount of a pharmaceutical composition comprising an isolated polypeptide of up to 50 amino acid comprising a sequence sharing at least 95% identity with the sequence set forth in SEQ ID NO: 1, SEQ ID NO: 2, SEQ ID NO: 3 or SEQ ID NO: 4, and said isolated polypeptide diminishes or abrogates an inflammatory response in the subject.

2. The method according to claim 1, wherein said subject suffers from systemic lupus erythematosus (SLE), multiple sclerosis, arthritis, asthma, inflammatory bowel disease, Crohn's disease, or psoriasis.

3. The method according to claim 2, wherein said subject suffers from systemic lupus erythematosus (SLE).

4. The method according to claim 2, wherein said subject suffers from multiple sclerosis.

5. The method according to claim 2, wherein said subject suffers from psoriasis.

6. The method according to claim 1, wherein said subject suffers from Parkinson's disease, amyotrophic lateral sclerosis, or Alzheimer's disease.

7. The method according to claim 1 wherein said subject suffers from sepsis.

8. A method for treating inflammation in a subject in need thereof, said method comprising administering to a subject suffering from a disease selected from the group consisting of an autoimmune disease, a degenerative neurological disease, a degenerative muscle disease, graft rejection, graft versus host disease, allergy, a musculo-skeletal inflammation and sepsis a therapeutically effective amount of an isolated polypeptide of up to 50 amino acids comprising a sequence sharing at least 95% identity with the sequence set forth in SEQ ID NO: 1, SEQ ID NO: 2, SEQ ID NO: 3 or SEQ ID NO: 4.

9. The method according to claim 8, wherein said subject suffers from systemic lupus erythematosus (SLE), multiple sclerosis, arthritis, asthma, inflammatory bowel disease, Crohn's disease, or psoriasis.

10. The method according to claim 9, wherein said subject suffers from systemic lupus erythematosus (SLE).

11. The method according to claim 9, wherein said subject suffers from multiple sclerosis.

12. The method according to claim 9, wherein said subject suffers from psoriasis.

13. The method according to claim 8, wherein said subject suffers from Parkinson's disease, amyotrophic lateral sclerosis, or Alzheimer's disease.

14. The method according to claim 8, wherein said subject suffers from sepsis.

15. The method of claim 8, wherein said isolated polypeptide has a sequence sharing at least 97% identity with the sequence set forth in SEQ ID NO: 1.

16. The method of claim 8, wherein said isolated polypeptide has a sequence sharing at least 99% identity with the sequence set forth in SEQ ID NO: 1.

17. The method of claim 8, wherein said isolated polypeptide consists of the amino acid sequence set forth in SEQ ID NO: 1.

18. The method of claim 8, wherein said isolated polypeptide has a sequence sharing at least 97% identity with the sequence set forth in SEQ ID NO: 2.

19. The method of claim 8, wherein said isolated polypeptide has a sequence sharing at least 99% identity with the sequence set forth in SEQ ID NO: 2.

20. The method of claim 8, wherein said isolated polypeptide consists of the amino acid sequence set forth in SEQ ID NO: 2.

21. The method of claim 8, wherein said isolated polypeptide has a sequence sharing at least 97% identity with the sequence set forth in SEQ ID NO: 3 or 4.

22. The method of claim 8, wherein said isolated polypeptide has a sequence sharing at least 99% identity with the sequence set forth in SEQ ID NO: 3 or 4.

23. The method of claim 8, wherein said isolated polypeptide consists of the amino acid sequence set forth in SEQ ID NO: 3 or 4.

* * * * *